United States Patent
McClung et al.

(10) Patent No.: US 11,896,393 B1
(45) Date of Patent: Feb. 13, 2024

(54) WEARABLE DIAGNOSTIC ELECTROCARDIOGRAM GARMENT

(71) Applicant: CB Innovations, LLC, Escondido, CA (US)

(72) Inventors: Christian McClung, Rancho Santa Fe, CA (US); Stephen Dunphy, Carlsbad, CA (US)

(73) Assignee: CB Innovations, LLC, Escondido, CA (US)

( * ) Notice: Subject to any disclaimer, the term of this patent is extended or adjusted under 35 U.S.C. 154(b) by 577 days.

(21) Appl. No.: 16/812,330

(22) Filed: Mar. 8, 2020

Related U.S. Application Data

(63) Continuation-in-part of application No. 15/990,651, filed on May 27, 2018, now Pat. No. 10,881,313, which is a continuation-in-part of application No. 15/853,578, filed on Dec. 22, 2017, now Pat. No. 9,986,929.

(60) Provisional application No. 62/825,018, filed on Mar. 27, 2019, provisional application No. 62/819,025, filed on Mar. 15, 2019, provisional application No. 62/530,144, filed on Jul. 8, 2017, provisional application No. 62/465,752, filed on Mar. 1, 2017.

(51) Int. Cl.
| | |
|---|---|
| *A41D 13/12* | (2006.01) |
| *A61B 5/00* | (2006.01) |
| *A41D 7/00* | (2006.01) |
| *A41D 1/00* | (2018.01) |
| *A41B 1/00* | (2006.01) |
| *A61B 5/30* | (2021.01) |

(52) U.S. Cl.
CPC .............. *A61B 5/6804* (2013.01); *A41B 1/00* (2013.01); *A41D 1/005* (2013.01); *A41D 7/008* (2013.01); *A61B 5/0006* (2013.01); *A61B 5/303* (2021.01)

(58) Field of Classification Search
CPC ..... A61B 5/6804; A61B 5/303; A61B 5/1006; A41B 1/00; A41B 1/1005; A41B 7/008
See application file for complete search history.

(56) References Cited

U.S. PATENT DOCUMENTS

| | | | |
|---|---|---|---|
| 4,121,575 A | 10/1978 | Mills et al. | |
| 4,202,344 A * | 5/1980 | Mills .................... | A61B 5/6831 600/382 |

(Continued)

FOREIGN PATENT DOCUMENTS

| | | |
|---|---|---|
| EP | 3001948 | 4/2016 |
| JP | S57175979 | 10/1982 |
| WO | WO2016029106 | 2/2016 |

OTHER PUBLICATIONS

Intl. Search Report PCT/US2018/019682, dated May 15, 2018.
European Patent Office Search Report for EP application 18757133.6, dated Nov. 17, 2020.

*Primary Examiner* — Richale L Quinn
(74) *Attorney, Agent, or Firm* — Clause Eight; Michael Catania

(57) ABSTRACT

A wearable diagnostic electrocardiogram (ECG) garment is disclosed herein. The wearable diagnostic ECG garment comprises a garment body, a plurality of electrodes positioned on the body, each of the plurality of electrodes comprising a connection stud, a contact pad interface and a contact pad, an electrode connector extending from the body, and a plurality of wires positioned in the garment (Continued)

body, each of the plurality of wires connected from the electrode connector to an electrode of the plurality of electrodes.

18 Claims, 19 Drawing Sheets

(56) References Cited

U.S. PATENT DOCUMENTS

| | | | |
|---|---|---|---|
| 4,233,987 A | 11/1980 | Feingold | |
| 4,498,480 A * | 2/1985 | Mortensen | A61B 5/6831 600/383 |
| 4,608,987 A * | 9/1986 | Mills | A61B 5/282 600/389 |
| 5,224,479 A * | 7/1993 | Sekine | A61B 5/282 600/389 |
| 6,006,125 A | 12/1999 | Kelly et al. | |
| 6,141,575 A | 10/2000 | Price | |
| 6,157,851 A | 12/2000 | Kelly et al. | |
| 6,173,198 B1 | 1/2001 | Schulze et al. | |
| 6,205,346 B1 | 3/2001 | Akiva | |
| 6,219,568 B1 | 4/2001 | Kelly et al. | |
| 6,219,569 B1 | 4/2001 | Kelly et al. | |
| 6,360,119 B1 | 3/2002 | Roberts | |
| 6,385,473 B1 | 5/2002 | Haines et al. | |
| 6,400,975 B1 | 6/2002 | McFee | |
| 6,400,977 B1 | 6/2002 | Kelly et al. | |
| 6,408,200 B1 * | 6/2002 | Takashina | A61B 5/6831 600/382 |
| 6,415,169 B1 | 7/2002 | Kornrumpf et al. | |
| 6,453,186 B1 | 9/2002 | Lovejoy et al. | |
| 6,456,872 B1 | 9/2002 | Faisandier | |
| 6,553,246 B1 | 4/2003 | Wenger | |
| 6,560,473 B2 | 5/2003 | Dominguez | |
| 6,567,680 B2 | 5/2003 | Swetlik et al. | |
| 6,611,705 B2 | 8/2003 | Hopman et al. | |
| 6,847,836 B1 * | 1/2005 | Sujdak | A61B 5/282 600/382 |
| 6,973,343 B2 | 12/2005 | Wenger | |
| 7,266,405 B1 | 9/2007 | Alroy et al. | |
| 7,272,428 B2 | 9/2007 | Hopman et al. | |
| 7,286,865 B2 | 10/2007 | Nazeri | |
| 7,299,084 B1 | 11/2007 | Price | |
| 7,395,106 B2 * | 7/2008 | Ryu | A61B 5/6804 600/388 |
| 7,403,808 B2 | 7/2008 | Istvan et al. | |
| 7,444,177 B2 | 10/2008 | Nazeri | |
| 7,860,557 B2 | 12/2010 | Istvan et al. | |
| 7,933,642 B2 | 4/2011 | Istvan et al. | |
| 8,175,674 B2 * | 5/2012 | Schmidt | A61B 5/282 600/393 |
| 8,180,425 B2 | 5/2012 | Selvitelli et al. | |
| 8,238,996 B2 | 8/2012 | Burnes et al. | |
| 8,251,736 B2 | 8/2012 | McIntire et al. | |
| 8,255,041 B2 | 8/2012 | Istvan et al. | |
| 8,369,924 B1 | 2/2013 | Chang | |
| 8,560,043 B2 | 10/2013 | Selvitelli et al. | |
| 8,571,627 B2 | 10/2013 | Tremblay et al. | |
| 8,608,984 B1 * | 12/2013 | Taranekar | A61B 5/6891 252/514 |
| 8,611,980 B2 | 12/2013 | Choe et al. | |
| 8,620,402 B2 | 12/2013 | Parker, III et al. | |
| 8,626,262 B2 | 1/2014 | McGusty et al. | |
| 8,660,630 B2 | 2/2014 | Chang | |
| 8,668,651 B2 | 3/2014 | Burnes et al. | |
| D702,356 S | 4/2014 | Vosch et al. | |
| 8,731,632 B1 | 5/2014 | Sereboff et al. | |
| 8,738,112 B2 | 5/2014 | Choe et al. | |
| 8,818,478 B2 * | 8/2014 | Scheffler | A41D 13/1281 600/509 |
| 8,818,482 B2 | 8/2014 | Phillips et al. | |
| 8,868,152 B2 | 10/2014 | Burnes et al. | |
| 8,868,216 B2 * | 10/2014 | Dunagan | A61B 5/6804 607/152 |
| 8,954,129 B1 * | 2/2015 | Schlegel | A61B 5/282 600/382 |
| 9,072,444 B2 | 7/2015 | Burnes et al. | |
| 9,339,202 B2 * | 5/2016 | Brockway | A61B 5/259 |
| 9,408,547 B2 | 8/2016 | Zhou et al. | |
| 9,433,367 B2 | 9/2016 | Felix et al. | |
| 9,433,380 B1 | 9/2016 | Bishay et al. | |
| 9,545,204 B2 | 1/2017 | Bishay et al. | |
| 9,545,228 B2 | 1/2017 | Bardy et al. | |
| 9,615,763 B2 | 4/2017 | Felix et al. | |
| 9,615,790 B2 | 4/2017 | Caprio et al. | |
| 9,642,537 B2 | 5/2017 | Felix et al. | |
| 9,655,537 B2 * | 5/2017 | Bardy | A61B 5/333 |
| 9,655,538 B2 | 5/2017 | Felix et al. | |
| 9,693,701 B2 | 7/2017 | Simpson | |
| 9,700,227 B2 | 7/2017 | Bishay et al. | |
| 9,705,239 B2 | 7/2017 | Cheng et al. | |
| 9,717,432 B2 | 8/2017 | Felix et al. | |
| 9,717,433 B2 | 8/2017 | Felix et al. | |
| 9,730,593 B2 | 8/2017 | Felix et al. | |
| 9,737,224 B2 | 8/2017 | Bardy et al. | |
| 9,737,226 B2 | 8/2017 | Zhou et al. | |
| 9,782,097 B2 | 10/2017 | Choe et al. | |
| 9,820,665 B2 | 11/2017 | Felix et al. | |
| 10,231,623 B2 * | 3/2019 | Varadan | H05K 1/038 |
| 10,893,818 B2 * | 1/2021 | McClung | A61B 5/282 |
| 11,141,091 B2 * | 10/2021 | Kumar | A61B 5/282 |
| 11,246,523 B1 * | 2/2022 | Abercrombie, II | H05K 5/0086 |
| 11,331,034 B2 * | 5/2022 | Rapin | A61B 5/7264 |
| 2002/0133069 A1 | 9/2002 | Roberts | |
| 2003/0191401 A1 | 10/2003 | Oury et al. | |
| 2004/0073104 A1 | 4/2004 | Brun del Re et al. | |
| 2004/0127802 A1 | 7/2004 | Istvan et al. | |
| 2005/0085736 A1 * | 4/2005 | Ambrose | A61B 5/282 600/509 |
| 2005/0113661 A1 | 5/2005 | Nazeri et al. | |
| 2005/0251003 A1 | 11/2005 | Istvan et al. | |
| 2005/0280531 A1 * | 12/2005 | Fadem | A61B 5/6833 600/323 |
| 2006/0030781 A1 | 2/2006 | Shennib | |
| 2006/0264725 A1 * | 11/2006 | Hannula | A61B 5/6804 600/340 |
| 2008/0009694 A1 | 1/2008 | Hartman | |
| 2008/0064970 A1 | 3/2008 | Montplaisir | |
| 2008/0114232 A1 * | 5/2008 | Gazit | A61B 5/282 600/390 |
| 2008/0154110 A1 | 6/2008 | Burnes et al. | |
| 2008/0287769 A1 | 11/2008 | Kurzweil et al. | |
| 2009/0253975 A1 | 10/2009 | Tiegs et al. | |
| 2009/0253996 A1 * | 10/2009 | Lee | A61B 5/16 600/544 |
| 2009/0270708 A1 * | 10/2009 | Shen | A61B 5/296 600/389 |
| 2010/0076295 A1 | 3/2010 | Peterson et al. | |
| 2010/0185076 A1 * | 7/2010 | Jeong | A41D 13/1281 600/388 |
| 2010/0198038 A1 * | 8/2010 | Nagata | A61B 5/282 29/846 |
| 2010/0292595 A1 | 11/2010 | Paul | |
| 2011/0092835 A1 | 4/2011 | Istvan et al. | |
| 2011/0237924 A1 * | 9/2011 | McGusty | A61B 5/335 600/391 |
| 2012/0226131 A1 | 9/2012 | Callahan et al. | |
| 2012/0323104 A1 | 12/2012 | Burnes et al. | |
| 2012/0330126 A1 * | 12/2012 | Hoppe | F16B 2/20 600/300 |
| 2013/0180054 A1 | 7/2013 | Huttula et al. | |
| 2013/0338472 A1 * | 12/2013 | Macia | A61B 5/02055 174/255 |
| 2014/0100465 A1 | 4/2014 | Kim et al. | |
| 2014/0296682 A1 | 10/2014 | Wada et al. | |
| 2014/0318699 A1 * | 10/2014 | Longinotti-Buitoni | H05K 1/038 156/247 |
| 2014/0373785 A1 | 12/2014 | Readinger et al. | |
| 2015/0065842 A1 | 3/2015 | Lee et al. | |
| 2015/0119677 A1 | 4/2015 | Liu | |
| 2015/0265177 A1 | 9/2015 | Burnes et al. | |

(56) References Cited

U.S. PATENT DOCUMENTS

| | | |
|---|---|---|
| 2016/0029906 A1 | 2/2016 | Tompkins et al. |
| 2016/0302726 A1 | 10/2016 | Chang |
| 2016/0310075 A1* | 10/2016 | Ross .................... A41C 3/02 |
| 2016/0367163 A1 | 12/2016 | Bishay et al. |
| 2017/0027468 A1 | 2/2017 | Huang et al. |
| 2017/0119305 A1 | 5/2017 | Bardy et al. |
| 2017/0156615 A1 | 6/2017 | Shirazi |
| 2017/0188871 A1 | 7/2017 | Bishay et al. |
| 2017/0209064 A1 | 7/2017 | Felix et al. |
| 2017/0238833 A1 | 8/2017 | Felix et al. |
| 2017/0251946 A1 | 9/2017 | Bardy et al. |
| 2017/0251948 A1 | 9/2017 | Felix et al. |
| 2017/0258358 A1 | 9/2017 | Bishay et al. |
| 2017/0273591 A1 | 9/2017 | Agus et al. |
| 2017/0303809 A1 | 10/2017 | Bishay et al. |
| 2017/0319094 A1 | 11/2017 | Felix et al. |
| 2017/0319095 A1 | 11/2017 | Felix et al. |
| 2018/0014780 A1* | 1/2018 | Sotzing .................. A61B 5/291 |
| 2018/0140225 A1* | 5/2018 | Gong ....................... G01B 7/16 |
| 2018/0271441 A1* | 9/2018 | Dabby ................... A41D 1/005 |
| 2018/0368495 A1* | 12/2018 | Simmons ........... A41D 13/1281 |
| 2020/0375537 A1* | 12/2020 | Carlile ..................... A61B 5/27 |
| 2021/0195732 A1* | 6/2021 | Longinotti-Buitoni ..................... D06M 15/564 |
| 2021/0315521 A1* | 10/2021 | Webster ................ A61B 5/318 |
| 2022/0013869 A1* | 1/2022 | Nunez Lopez ........ H05K 3/284 |

* cited by examiner

WEARABLE DIAGNOSTIC ELECTROCARDIOGRAM GARMENT

CROSS REFERENCES TO RELATED APPLICATIONS

The Present Application claims priority to U.S. Provisional Patent Application No. 62/819,025 filed on Mar. 15, 2019, and U.S. Provisional Patent Application No. 62/825,018 filed on Mar. 27, 2019, and is a continuation-in-part application of U.S. patent application Ser. No. 15/990,651, filed on May 27, 2018, which is a continuation application of U.S. patent application Ser. No. 15/853,578, filed on Dec. 22, 2017, now U.S. Pat. No. 9,986,929, issued on Jun. 5, 2018, which claims priority to U.S. Provisional Patent Application No. 62/465,752, filed on Mar. 1, 2017, and also claims priority to 62/530,144, filed on Jul. 8, 2017, each of which is hereby incorporated by reference in its entirety.

STATEMENT REGARDING FEDERALLY SPONSORED RESEARCH OR DEVELOPMENT

Not Applicable

BACKGROUND OF THE INVENTION

Field of the Invention

The present invention generally relates to ECG devices.

Description of the Related Art

The electrocardiogram (ECG) is an essential test that provides medical professionals with essential information in the management of patients with a variety of conditions. It is not only of significant importance in the evaluation and management of patients with chest pain, but also in patients with shortness of breath, syncope, dizziness, seizures, altered mental status, stroke, psychiatric conditions, overdose, palpitations and many other conditions. It is a bulky system with a multitude of wires and connections.

The ECG provides critical data to the health care provider in managing patients with multiple medical issues. The time to obtain this data is critical and often delayed by the current technology. Minutes can become critical in the patient with an acute myocardial infarction (heart attack).

Historically, there is training in the interpretation of ECG data, as well as placement of electrodes on the chest of each patient in anatomically specific positions.

Current ECG placement is done by technicians and providers of varying medical background, including paramedics, health care technicians, nursing assistants, nurses, and doctors. The current technology is bulky, with many wires and cables. The placement of the electrodes in the acquisition of an ECG is specific and requires special training. ECG acquisition is often limited and/or delayed by multiple factors such as body sweat, ability to transport the ECG device into confined areas, performance of concomitant medical procedures such as cardiopulmonary resuscitation (CPR). Because of many limitations, medical providers must make rapid decisions and potentially delay medical care while ECG testing is done. As emergency medicine providers, the inventors have identified a need for more rapid placement of the ECG electrodes, a more portable and manageable system that will not compromise medical care, and the need to eliminate electrode placement errors.

Sujdak, U.S. Pat. No. 6,847,836 for an Emergency ECG Electrode Chest Pad discloses a chest adapted for use in an emergency room.

Dominguez, U.S. Pat. No. 6,560,473 for a Disposable ECG Chest Electrode Template With Built-In Defibrillation Electrodes discloses a template that carries ten electrodes.

The acquisition of a 12-lead ECG requires accurate placement of electrodes and avoidance of lead transposition. This has been a challenge for many healthcare workers and staff that place ECG electrodes. For lay persons outside of the healthcare setting this requires expertise not typically expected of the general population. Heart disease is still the number one cause of death in the United States. With an ever-increasing aged population, the timely diagnosis of heart disease and risk stratification is key to improved morbidity and mortality. The 12-lead ECG is central to this diagnosis and management. Technology is enabling extension of the health care continuum to expand into the home and away from a hospital or clinical setting. With a population of educated patients that value time and utility of their health care data, the ability to transmit and interpret reliable ECG data outside of the standard health care setting allows patients to take even more ownership of their health.

BRIEF SUMMARY OF THE INVENTION

The motivation for the present invention is to make garments capable of making diagnostic electrocardiogram access to a population both within and outside traditional health care settings. Enable a diagnostic quality ECG to be obtained that conforms to American Heart Association guidelines on diagnostic resting ECGs and also capable of obtaining continuous diagnostic ECG monitoring and acquisition during times of exercise and exertion. The device allows for electrode placement in key positions that conform to proximal limb positions and precordial chest positions that allow for a diagnostic-quality ECG to be obtained. Further more the garment allows for this to be applied by both lay persons and medically trained staff.

Incorporation of ECG electrodes and conducting circuits into a wearable, stretchable and elastic garment with integrated electrical conducting materials that transfer physiologic electrical signals to a central processing unit for ECG acquisition and interpretation. Available in multiple sizes to accommodate different body types. Reusable. Washable. Durable. The device can be used repeatedly by the same user or multi-use between persons with similar sizing restraints.

The acquisition of a 12-lead ECG requires accurate placement of electrodes and avoidance of lead transposition. This has been a challenge for many healthcare workers and staff that place ECG electrodes. For lay persons outside of the healthcare setting this requires expertise not typically expected of the general population. Heart disease is still the number one cause of death in the United States. With an ever-increasing aged population, the timely diagnosis of heart disease and risk stratification is key to improved morbidity and mortality. The 12-lead ECG is central to this diagnosis and management. Technology is enabling extension of the health care continuum to expand into the home and away from a hospital or clinical setting. With a population of educated patients that value time and utility of their health care data, the ability to transmit and interpret reliable ECG data outside of the standard health care setting allows patients to take even more ownership of their health. The use of ECG-enabled garments also allows this data to be obtained sooner and more reliably among patients presenting to any triage situation whether that is in the pre-hospital setting or the setting of a crowded emergency room. Smart-garments with multi-sensor monitoring of key vital signs will help to address the dangers in recognizing which triaged patients are experiencing changes in vital signs that may signify more abrupt needs for care and resource allocation.

By incorporating a multitude of electrodes and conducting materials into a stretchable, elastic garment with indexed positions that meet American Heart Association diagnostic criteria for ECG analysis, connected to a central unit that transmits acquired electrical signals to an ECG algorithm monitor (with or without signal amplification) via wireless or wired technology to a cloud based data evaluation system and physician confirmed interpretation. By incorporation into a simple garment system it is assured to place electrodes in the indexed AHA recommended positions across various body types and ensure precise placement and meet diagnostic criteria for resting— and exertion— ECG analysis.

Emergency Cardiac and Electrocardiogram (ECG) electrode placement device is a worn device that incorporates elastic electrical conducting materials and elastic material into a pad that is applied to the chest wall placing the electrodes in the appropriate anatomic locations in a rapid, reproducible, reliable fashion. It is provided in a compact, easily stored and transported form, that is applied to the chest wall with materials that have adhesive capabilities that resist moisture and conforms to the body with inherent elasticity with placement of electrodes within the pad that maintain proper anatomic ratios and locations. This device remains adherent to the body for specific lengths of time, with examples including adherence for potentially a minimum of 48 hour, but remain easily removable, while tolerating physiologic changes such as sweat and fever and medical treatment such as CPR. The device is clearly marked and designed to fit to the chest wall so that its application ensures proper placement of all electrodes. The incorporated electrical conducting materials combine together into a single cable/wire that is either directly or indirectly joined to an ECG monitoring device. The cable has adaptor capability that allows for wireless transfer of data to an ECG monitoring device obviating the need for having a bulky ECG machine in close proximity to the patient. The single cable also eliminates the need for multiple wires on a patient. Multiple wires that could potentially interfere with diagnostic imaging such as chest radiographs, or interfere with placement of emergency medical equipment such as transcutaneous cardiac pacer pads or defibrillating pad.

One aspect of the present invention is an emergency cardiac and electrocardiogram (ECG) electrode garment.

Another aspect of the present invention is a wearable diagnostic electrocardiogram (ECG) garment comprising a garment body, electrodes, an electrode connector and wires. The electrodes are positioned on the body. Each of the electrodes comprises a connection stud, a contact pad interface and a contact pad. The electrode connector extends from the body. The wires are positioned in the garment body. Each of the wires is connected from the electrode connector to an electrode.

The garment is preferably a long sleeve shirt, a short sleeve shirt or a robe. The diagnostic ECG for the wearable diagnostic electrocardiogram garment conforms to the American Heart Association (AHA) guidelines. The wearable diagnostic electrocardiogram garment further comprises a wireless transmitter. The ten electrodes are indexed to meet AHA guidelines for diagnostic criteria 12-lead ECG and additional node positions for diagnostic studies for right sided interpretation and posterior interpretation lead positioning.

Another aspect of the present invention is a wearable diagnostic electrocardiogram (ECG) garment comprising a garment body, electrodes, an electrode connector and printed wires. The electrodes are positioned on the body. Each of the electrodes comprises a connection stud, a contact pad interface and a contact pad. The printed wires are printed on the garment body. Each of the printed wires is connected from the electrode connector to an electrode of the plurality of electrodes.

Having briefly described the present invention, the above and further objects, features and advantages thereof will be recognized by those skilled in the pertinent art from the following detailed description of the invention when taken in conjunction with the accompanying drawings.

DETAILED DESCRIPTION OF THE INVENTION

Figure 1:
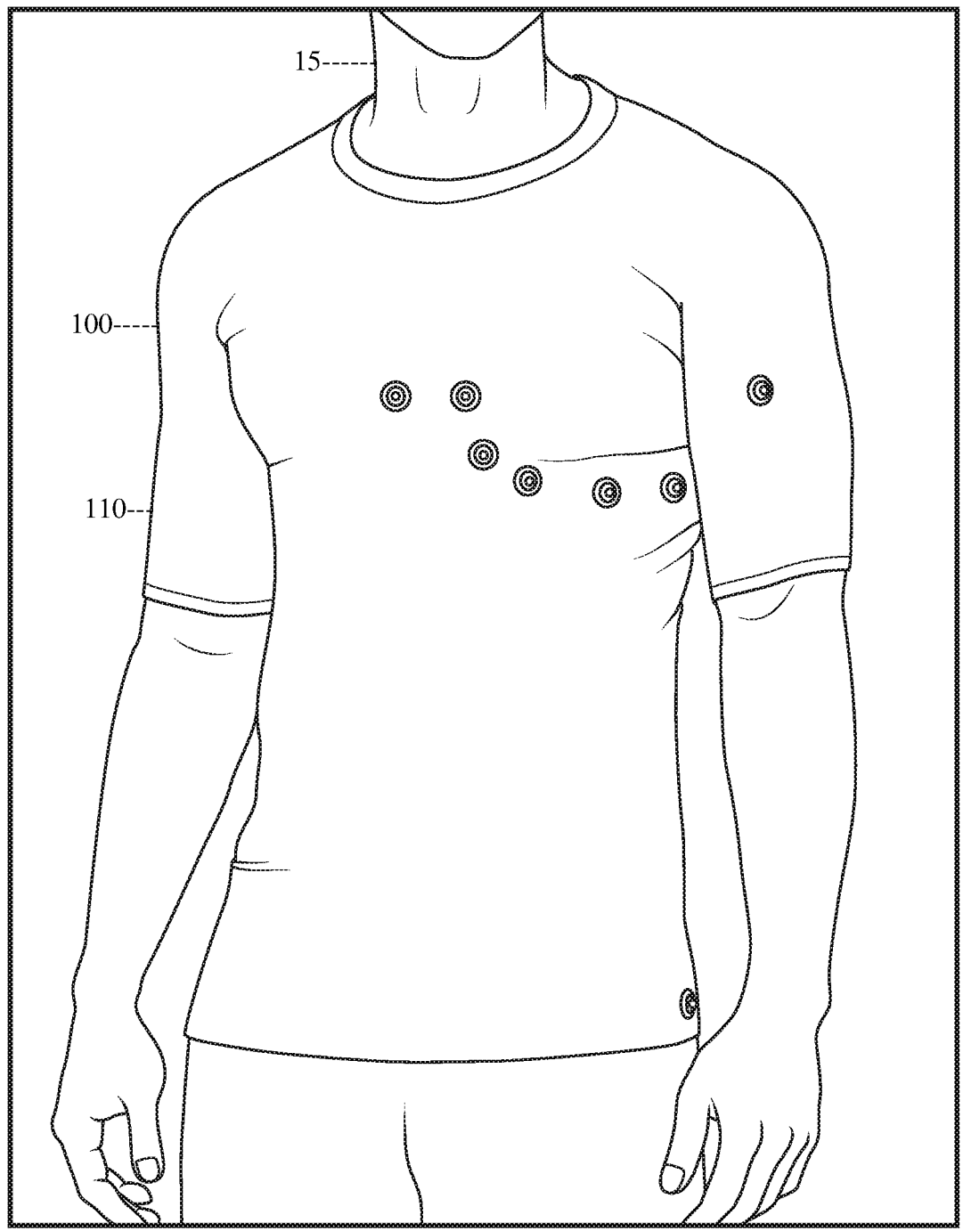
FIG. 1 illustrates a shirt embodiment of the emergency cardiac and ECG electrode device.
Figure 1A:
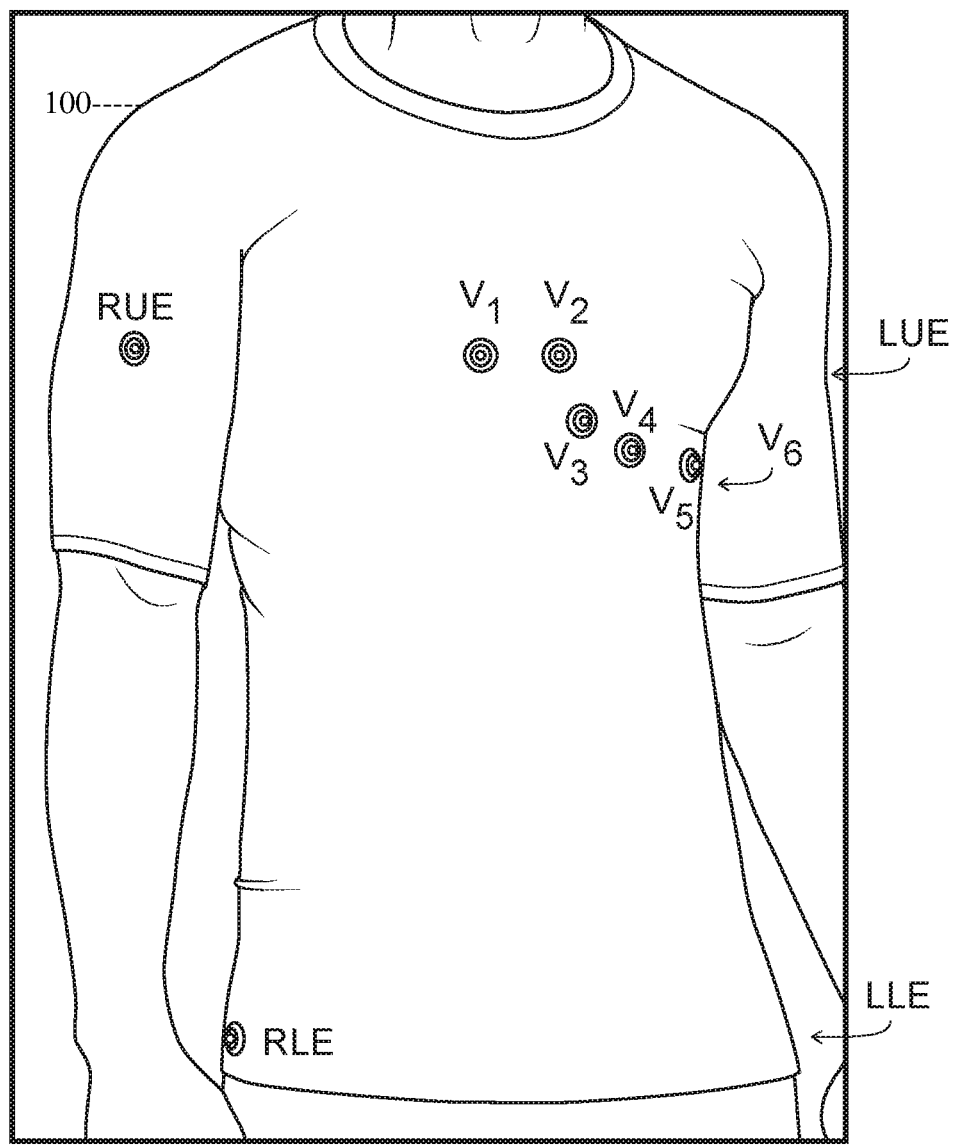
FIG. 1A illustrates a shirt embodiment of the emergency cardiac and ECG electrode device.
Figure 2:
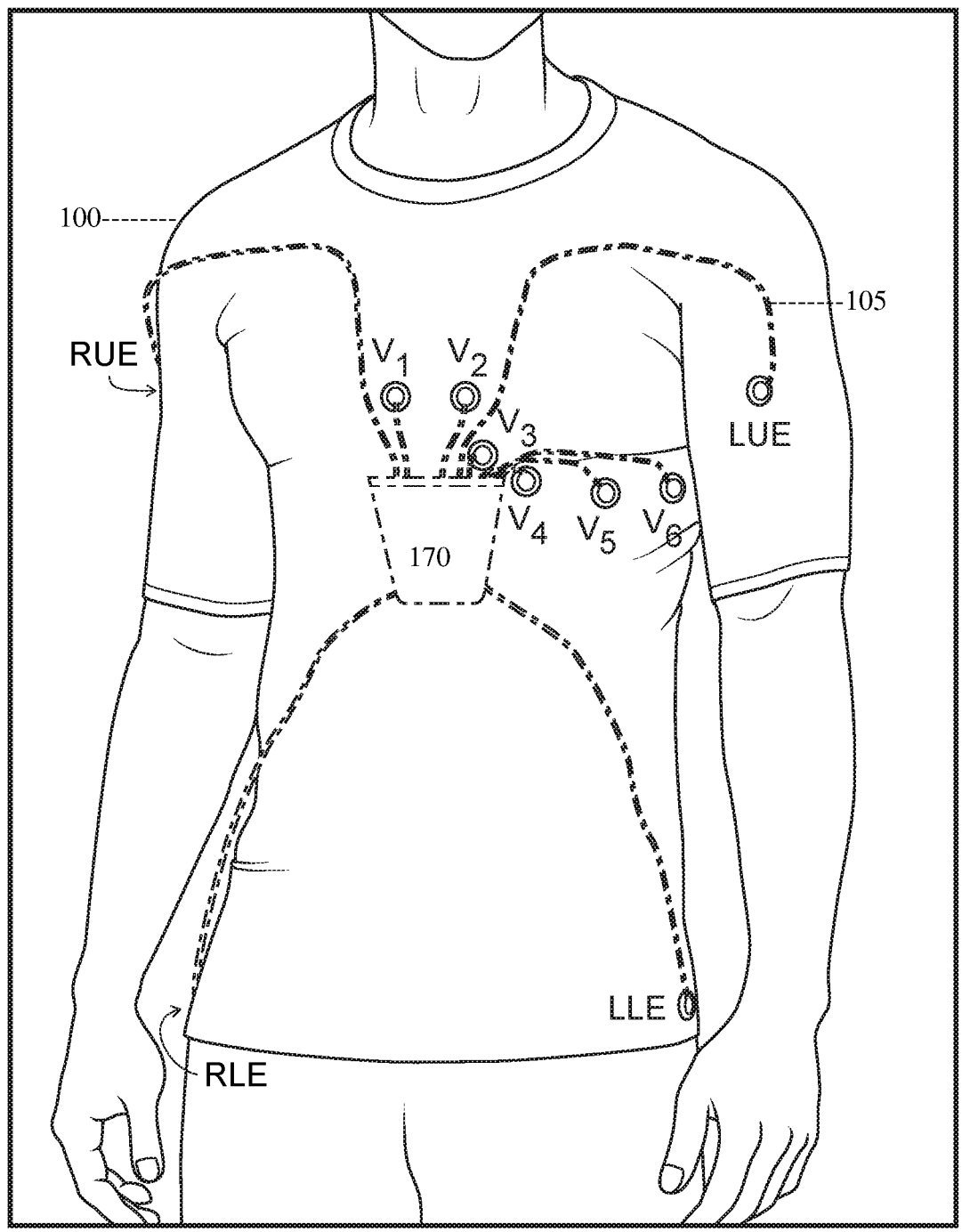
FIG. 2 illustrates a shirt embodiment of the emergency cardiac and ECG electrode device.

As shown in FIGS. 1, 1A and 2, a wearable diagnostic electrocardiogram (ECG) garment 100 worn by a user 15 comprises a garment body 110, electrodes V1-V6, an electrode connector 170 and wires 105. The electrodes are positioned on the body 110. Each of the electrodes comprises a connection stud, a contact pad interface and a contact pad. The electrode connector 170 preferably extends from the body 110. The wires 105 are positioned in the garment body 110. Each of the wires 105 is connected from the electrode connector 170 to an electrode V1-V6.

Figure 3:
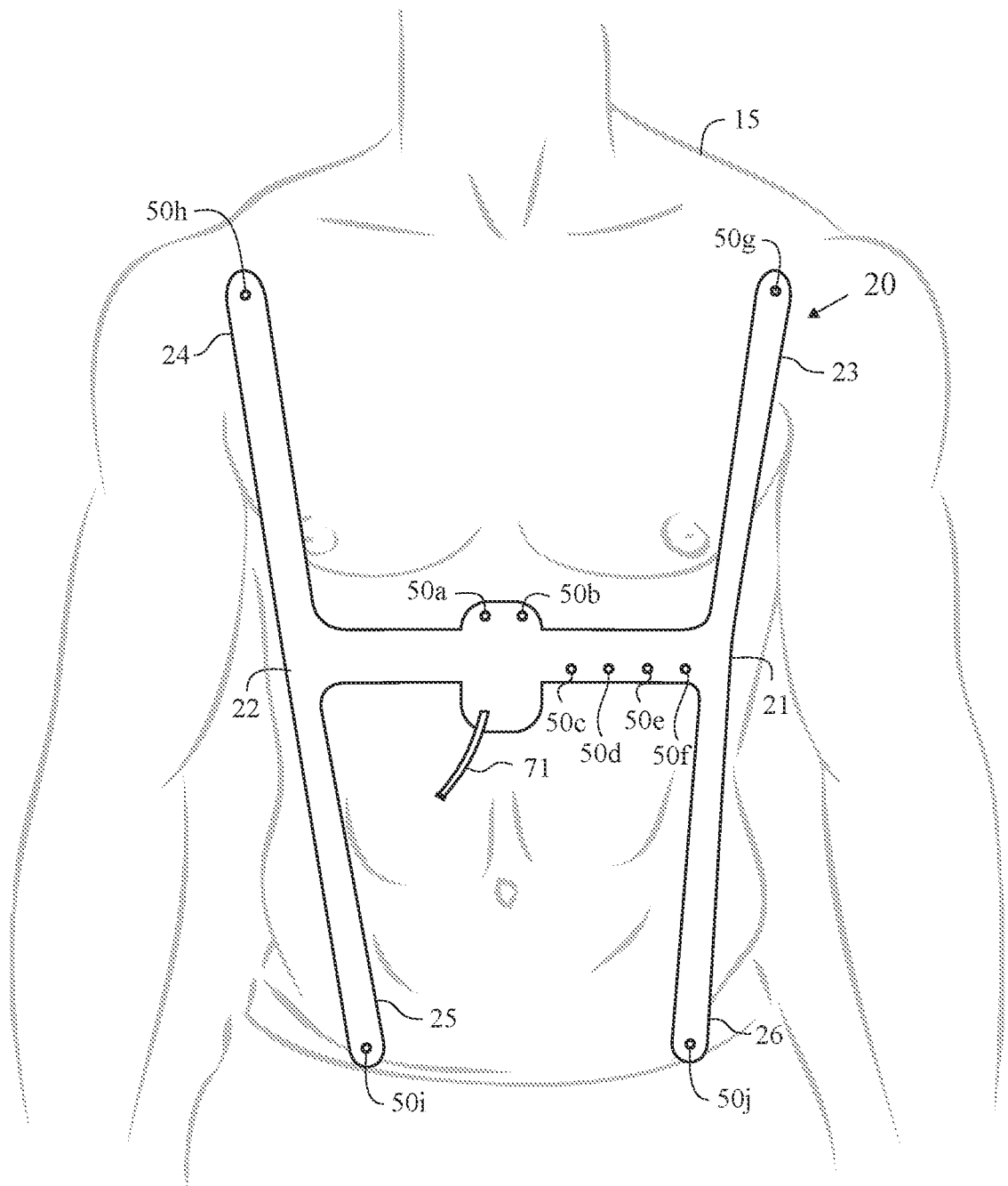
FIG. 3 is an illustration of a first embodiment of an emergency cardiac and ECG electrode placement device positioned on a patient.
Figure 3A:
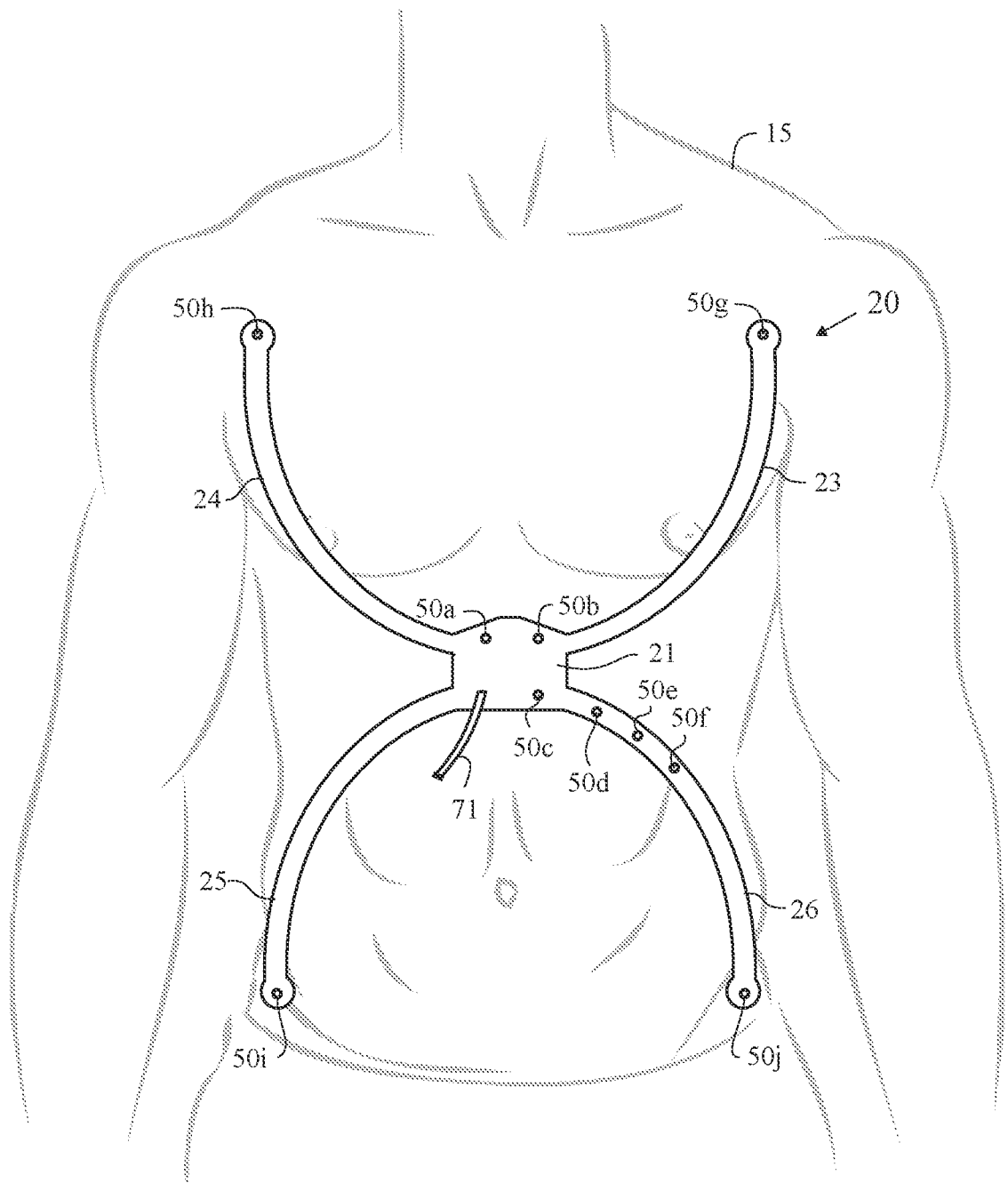
FIG. 3A is an illustration of a second embodiment of an emergency cardiac and ECG electrode placement device positioned on a patient.
Figure 3B:
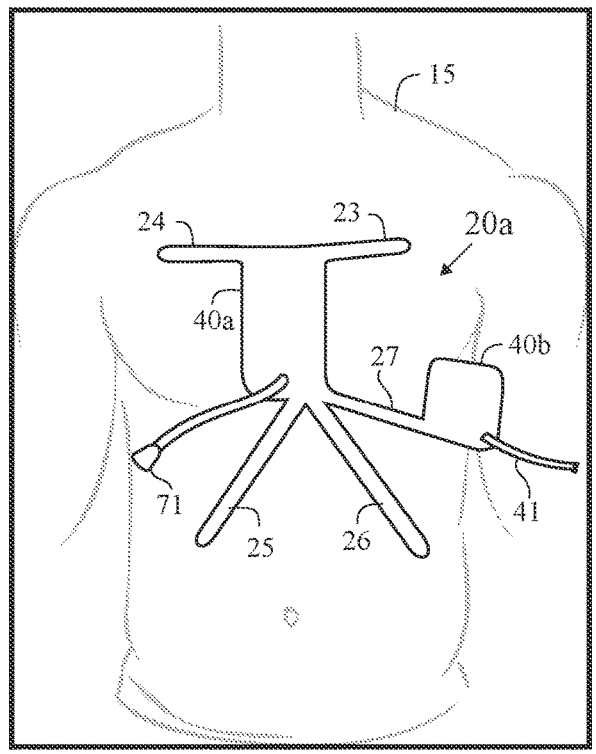
FIG. 3B is an illustration of a third embodiment of an emergency cardiac and ECG electrode placement device with a defibrillation mechanism positioned on a patient.
Figure 3C:
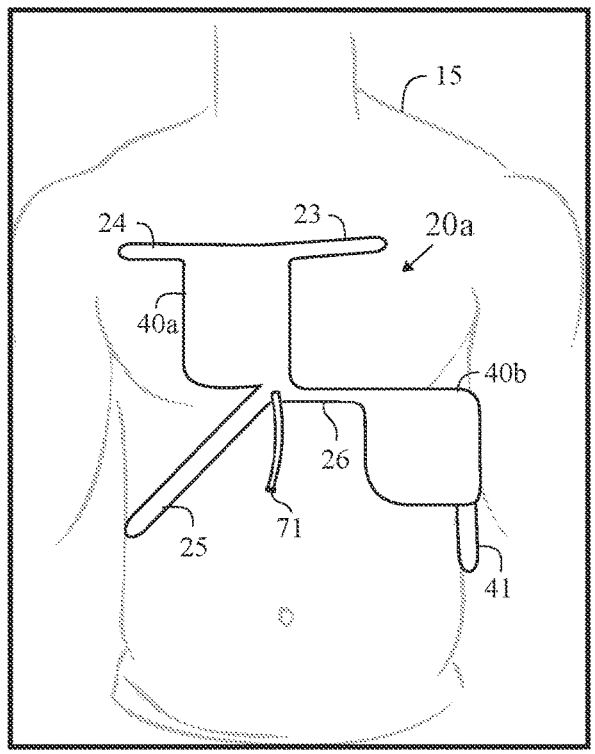
FIG. 3C is an illustration of a fourth embodiment of an emergency cardiac and ECG electrode placement device with a defibrillation mechanism positioned on a patient.
Figure 3D:
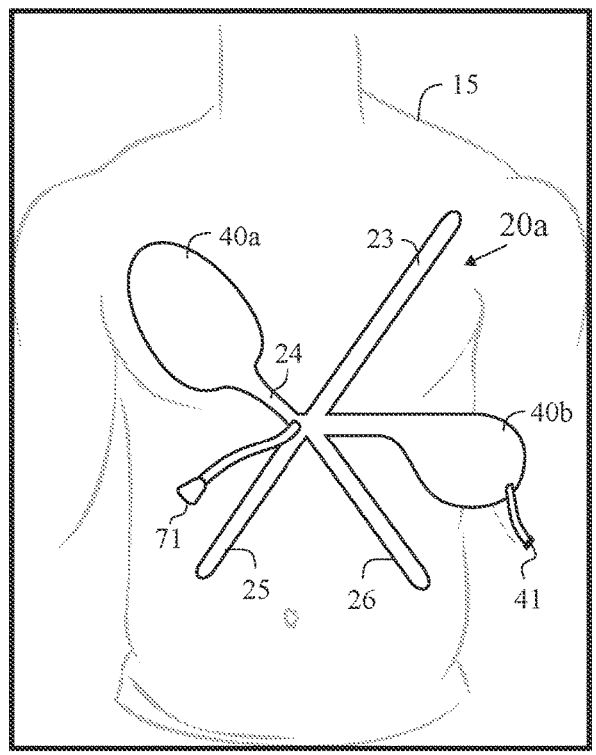
FIG. 3D is an illustration of a fifth embodiment of an emergency cardiac and ECG electrode placement device with a defibrillation mechanism positioned on a patient.
Figure 3E:
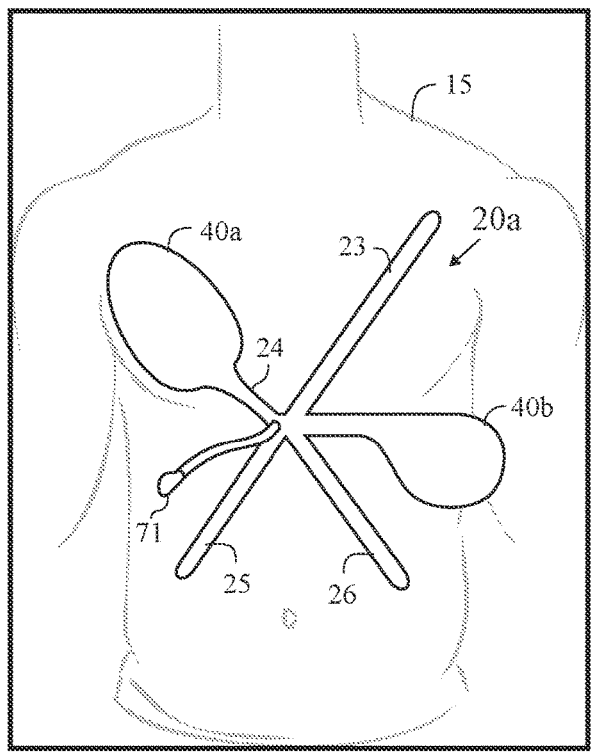
FIG. 3E is an illustration of a sixth embodiment of an emergency cardiac and ECG electrode placement device with a defibrillation mechanism positioned on a patient.
Figure 4:
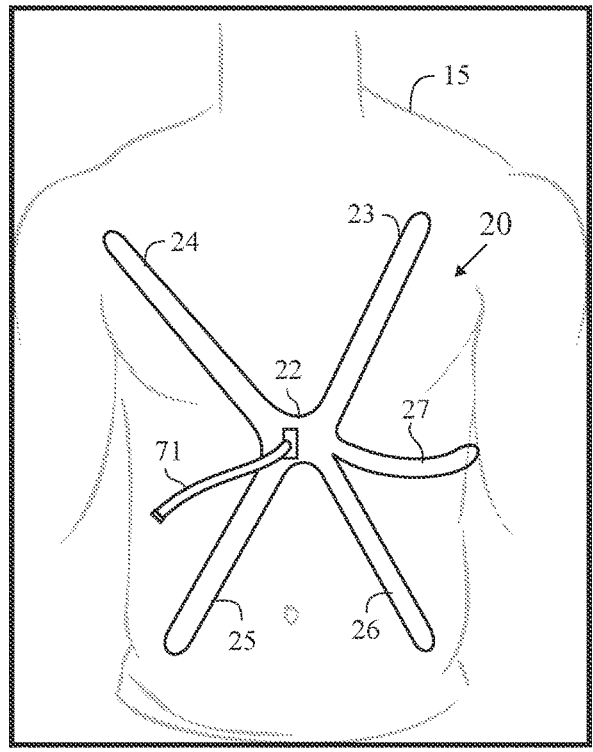
FIG. 4 is an illustration of a seventh embodiment of an emergency cardiac and ECG electrode placement device positioned on a patient.
Figure 4A:
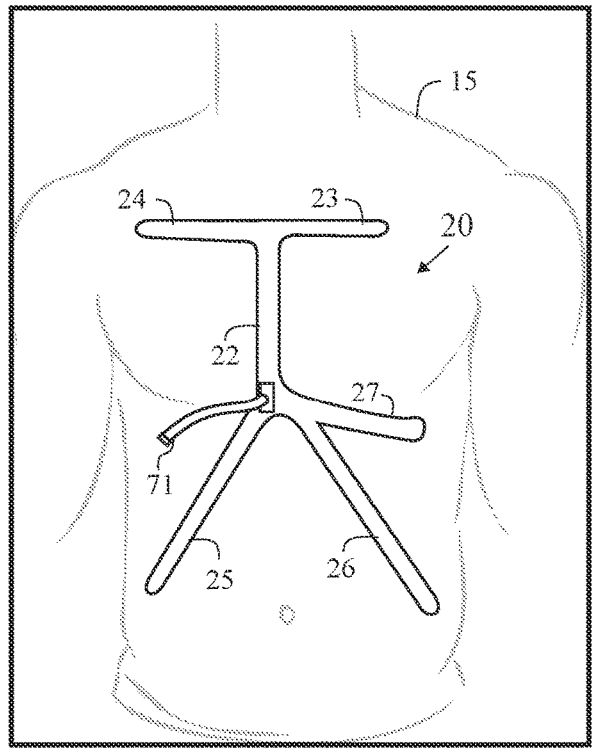
FIG. 4A is an illustration of an eighth embodiment of an emergency cardiac and ECG electrode placement device positioned on a patient vice.
Figure 4B:
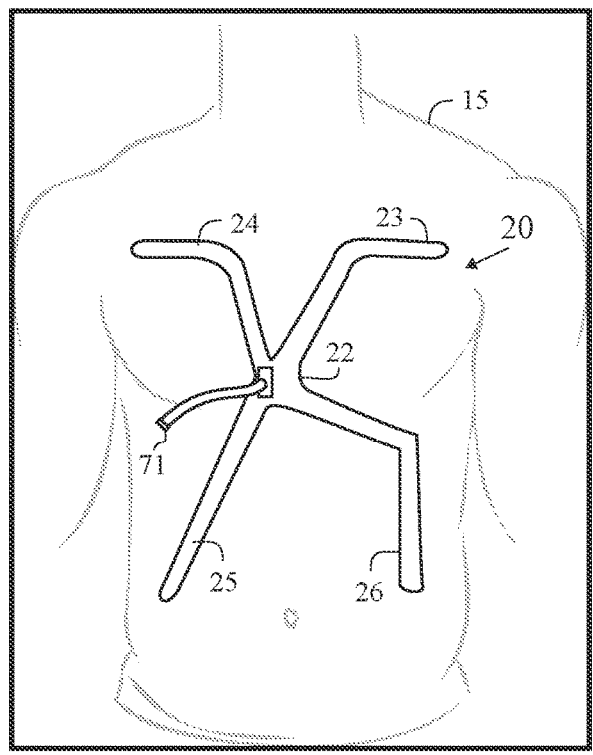
FIG. 4B is an illustration of a ninth embodiment of an emergency cardiac and ECG electrode placement device positioned on a patient.
Figure 4C:
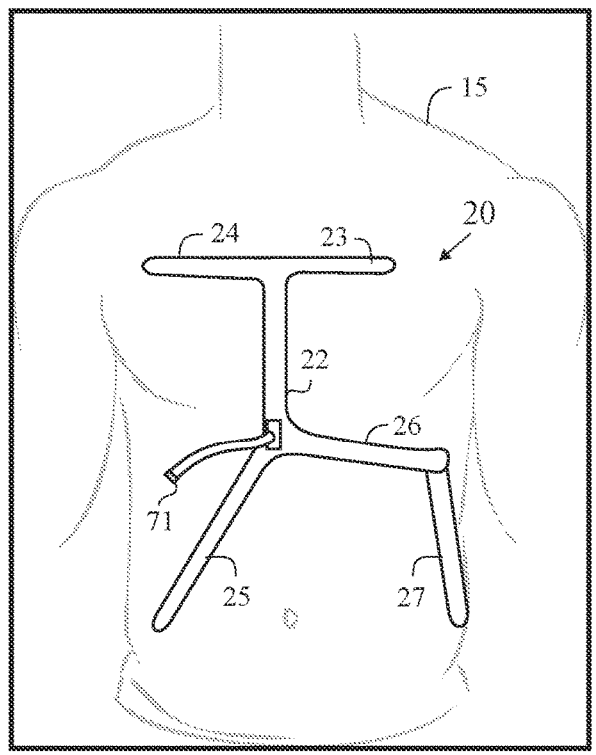
FIG. 4C is an illustration of a tenth embodiment of an emergency cardiac and ECG electrode placement device positioned on a patient.
Figure 5:
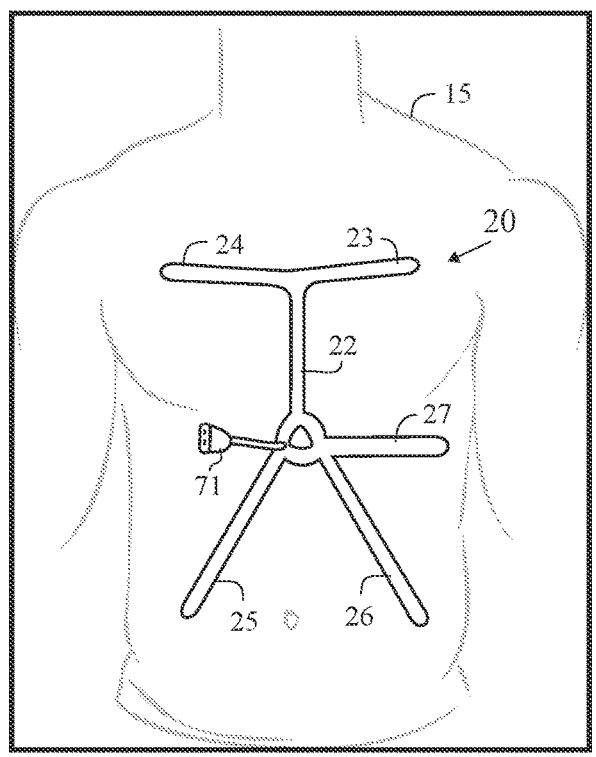
FIG. 5 is an illustration of an eleventh embodiment of an emergency cardiac and ECG electrode placement device positioned on a patient.
Figure 5A:
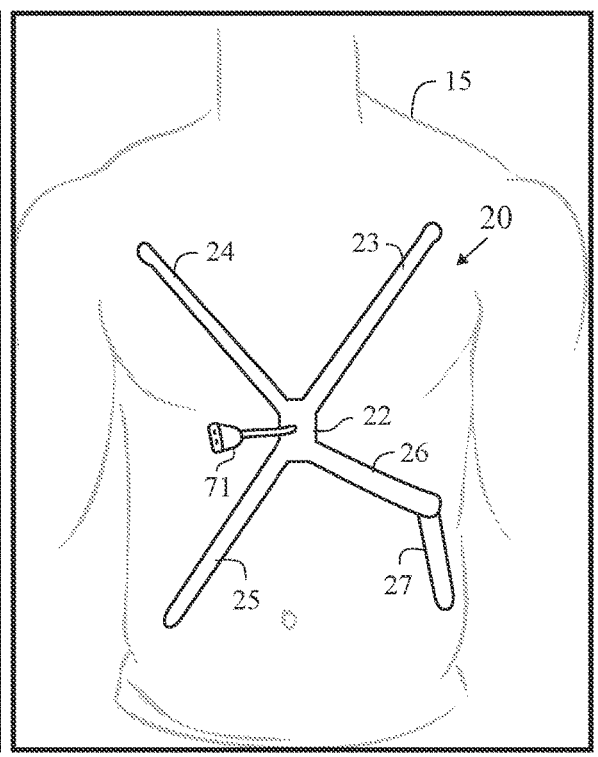
FIG. 5A is an illustration of a twelfth embodiment of an emergency cardiac and ECG electrode placement device positioned on a patient.

As shown in FIG. 3, an EXG device 20 preferably comprises a body 21, electrodes 50, printed wires or an electrical conducting flexible material 60 (not shown), and an electrode cable connector 71. The body 21 preferably comprises a center extension member 22, a first extension member 23, a second extension member 24, a third extension member 25 and a fourth extension member 26. The electrode cable connector 71 is positioned on the body 21. Each extension member 22-26 preferably has a width ranging from 1 cm to 10 cm, and a length ranging from 5 cm to 20 cm. The center extension member 22 preferably comprises a first electrode 50a, a second electrode 50b, a third electrode 50c, a fourth electrode 50d, a fifth electrode 50e and a sixth electrode 50f. Printed wires or electrical conducting flexible material 60 (not shown) connect each electrode 50 to the electrode cable connector 71.

Other embodiments of EXG device 20 are shown in FIGS. 4, 4A, 4B, 4C, and 5A. The extension members extend outward from the center of the body 21.

Figure 10:
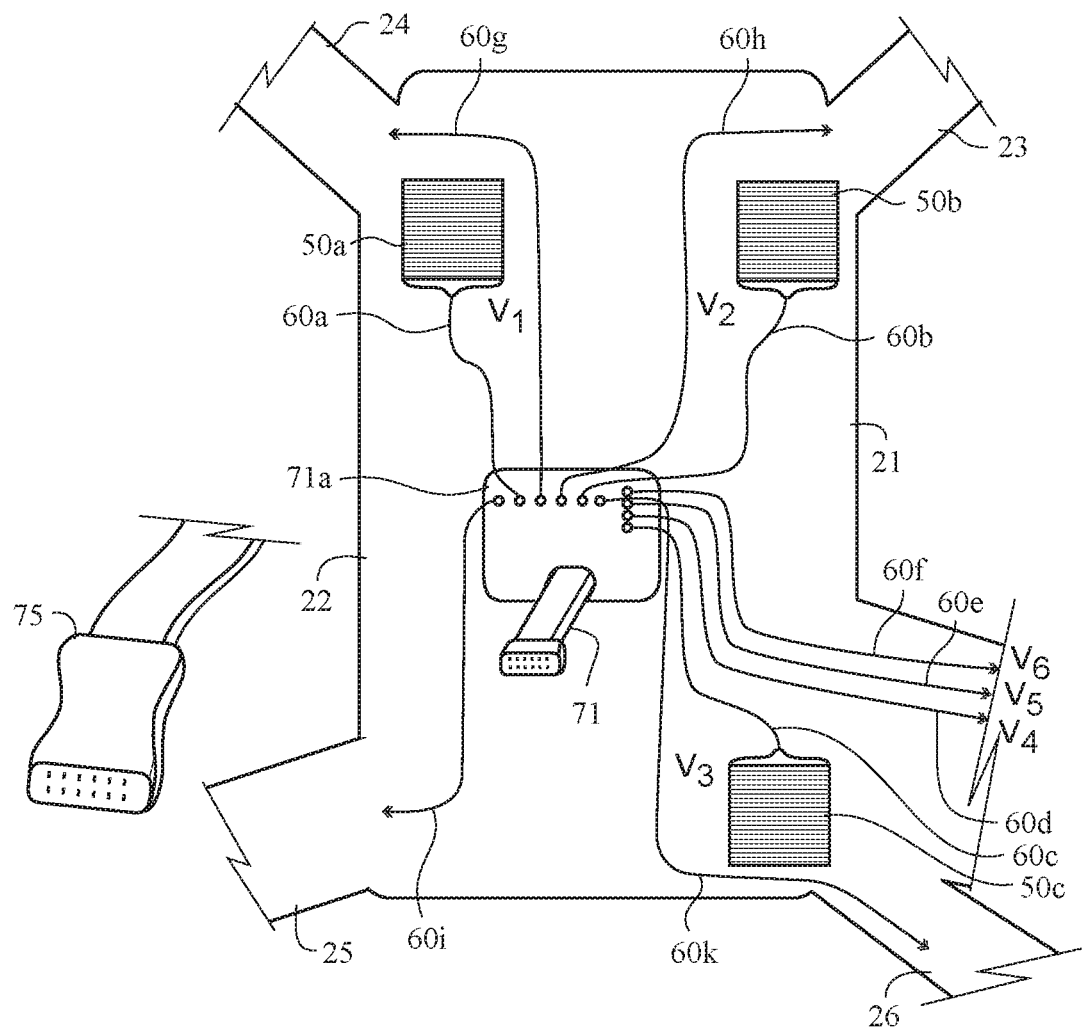
FIG. 10 is an isolated view of a portion of an emergency cardiac and ECG electrode placement device.

As shown in FIG. 10, a printed wire 60a connects the electrode 50a to the electrode cable connector 71. A printed wire 60b connects the electrode 50b to the electrode cable connector 71. A printed wire 60c connects the electrode 50c to the electrode cable connector 71. A printed wire 60d connects the electrode 50d to the electrode cable connector 71. A printed wire 60e connects the electrode 50e to the electrode cable connector 71. A printed wire 60f connects the electrode 50f to the electrode cable connector 71. A printed wire 60g connects the electrode 50g to the electrode cable connector 71. A printed wire 60h connects the electrode 50h to the electrode cable connector 71. A printed wire 60i connects the electrode 50i to the electrode cable connector 71. A printed wire 60j connects the electrode 50j to the electrode cable connector 71. A ten pin electrode interface 75 connects to the electrode cable connector 71. On one embodiment, the elastic electrically conductive material is preferably applied with a 3D printer directly on the main layer.

Alternatively, an elastic conductive material is substituted for each of the printed wires in FIG. 10. Such elastic conductive materials preferably comprise silver chloride and/or graphene. The body 21 is preferably composed of a kinesiology type tape.

Alternative embodiments of the EXG device 20a shown in FIGS. 3A, 3B, 3C, 3D and 3E also comprise integrated defibrillation pads 40a and 40b connected to a defibrillation cable 41. In the unstable patient, defibrillation becomes a crucial aspect of emergency cardiac care. The use of defibrillation pads has in the field historically been done with pad placement at the discretion of the first responder/paramedic. The most common deployment being anteriorly. This often leads to suboptimal placement and suboptimal delivery of electricity. The EXG-DF with defibrillator pad assures proper placement of the device in the anterior posterior configuration, which allows for optimal electrical conductance to the heart. The vector of electrical conductance is optimally placed in an anterior posterior configuration. There is no device that provides optimal defibrillator pad placement while integrating twelve lead EKG ability with ability to extend to include posterior and right sided lead EKG. The ability to obtain instant EKG data after critical defibrillation has heretofore been impractical for the pre-hospital care provider. The EXG-DF-DF addresses this critical issue in cardiac care.

Figure 6:
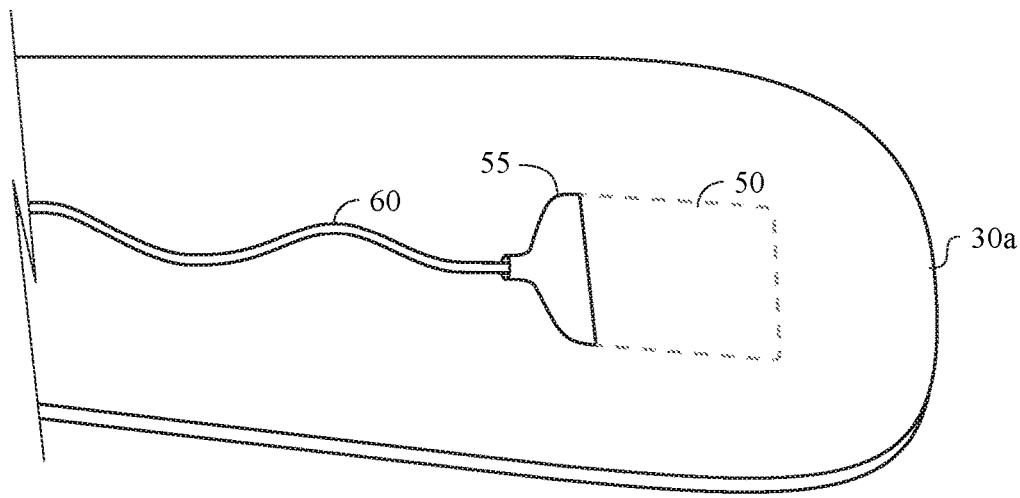
FIG. 6 is an isolated top perspective view of a top surface of an extension of an emergency cardiac and ECG electrode placement device.

FIG. 6 illustrates an isolated top perspective view of a top surface of an extension of the EXG device 20. The extension has a top layer 30a with an integrated printed wire (or elastic electrical conducting material) 60 connected to an electrode interface 55 integrated with an electrode 50 that is positioned on an adhesive surface below. The electrode 50 is not positioned on the top surface 30a of the main layer 30.

Figure 7:
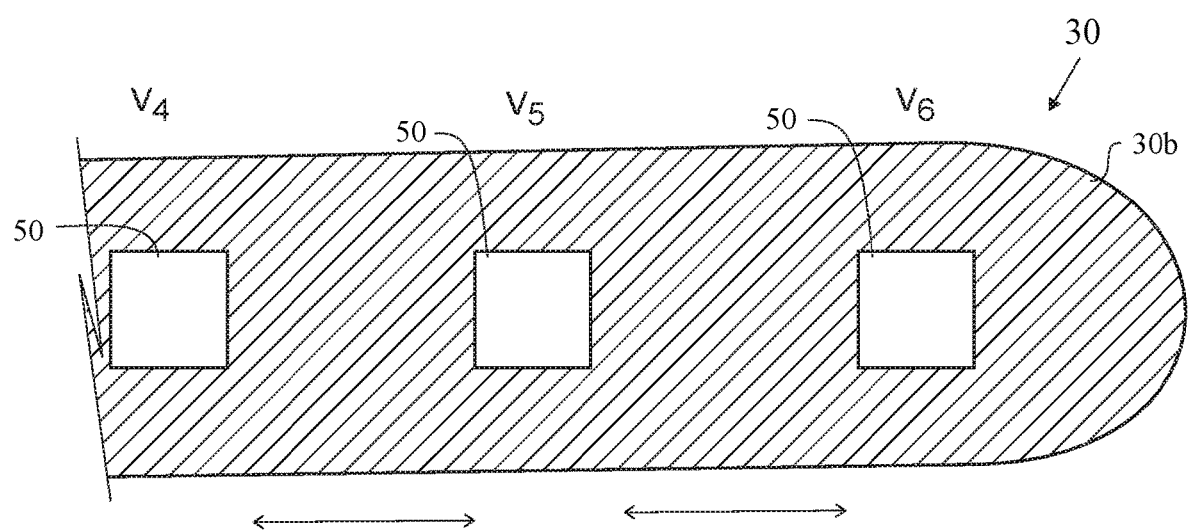
FIG. 7 is an isolated bottom plan view of a bottom surface of an extension of an emergency cardiac and ECG electrode placement device.

FIG. 7 illustrates an isolated bottom plan view of a bottom surface of an extension of an EXG device 20. On bottom adhesive surface 30b of the main layer 30 has electrodes 50 positioned thereon.

Figure 8:
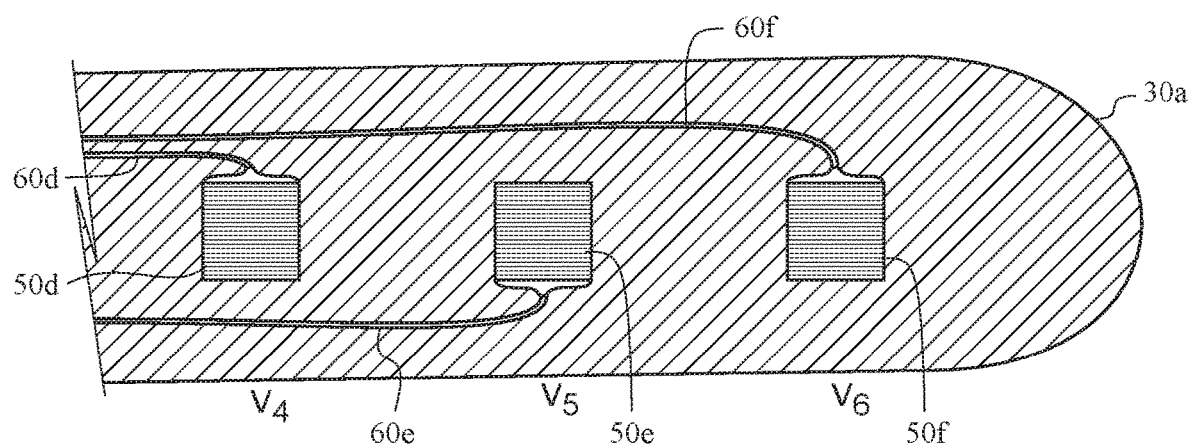
FIG. 8 is an isolated top plan view of a top surface of an extension of an emergency cardiac and ECG electrode placement device.

FIG. 8 illustrates an isolated top plan view of a top surface of an extension of the EXG device 20. The main layer 30 of the extension has a top layer 30a with an integrated printed wires (or elastic electrical conducting material) 60d, and 60f connected to corresponding electrodes 50d, 50e and 50f that are positioned on an adhesive surface below. The electrodes 50d, 50e and 50f are not positioned on the top surface 30a of the main layer 30.

Figure 9:
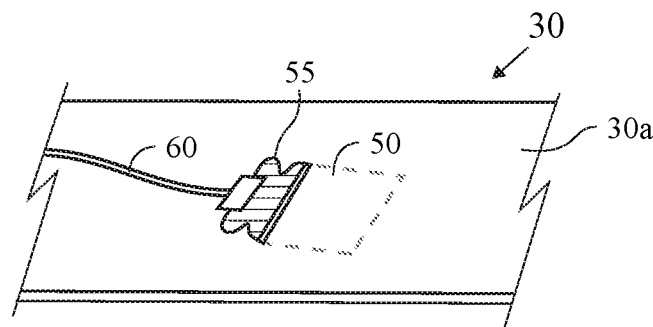
FIG. 9 is an isolated top perspective view of a top surface of an extension of an emergency cardiac and ECG electrode placement device.

FIG. 9 is an isolated top perspective view of a top surface of an extension of the EXG device 20. The extension has a top layer 30a with an integrated printed wire (or elastic electrical conducting material) 60 connected to an electrode interface 55 integrated with an electrode 50 that is positioned on an adhesive surface below. The electrode 50 is not positioned on the top surface 30a of the main layer 30

Figure 9A:
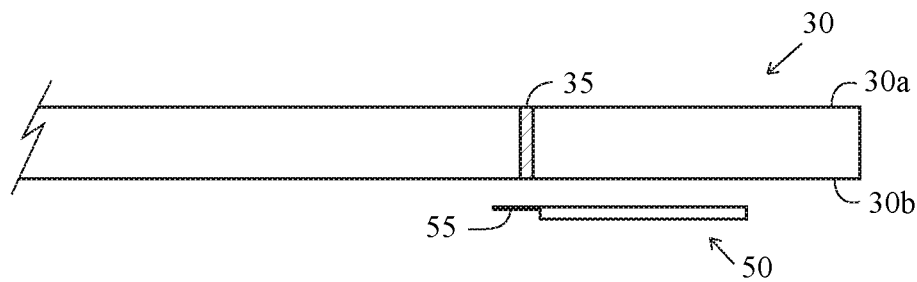
FIG. 9A is an isolated exploded cross-sectional view of the extension of an emergency cardiac and ECG electrode placement device of FIG. 9 and an electrode.

FIG. 9A is an isolated exploded cross-sectional view of the extension of the EXG device 20 of FIG. 9 and an electrode 50. The interface 55 is placed through an aperture 35 in the main layer 30 to connect to the integrated printed wire (or elastic electrical conducting material) 60.

Figure 9B:
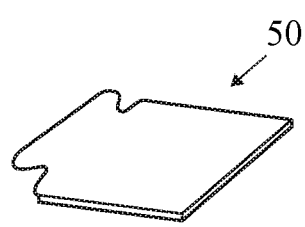
FIG. 9B is an isolated bottom view of an electrode for an emergency cardiac and ECG electrode placement device.

FIG. 9B is an isolated bottom view of an electrode 50 for an EXG device 20.

Figure 9C:
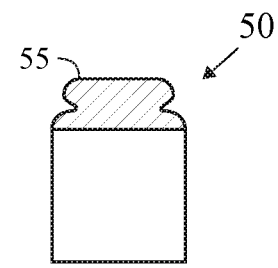
FIG. 9C is an isolated top view of an electrode for an emergency cardiac and ECG electrode placement device.

FIG. 9C is an isolated top view of an electrode 50 with an interface 55 for an EXG device 20. The interface is preferably composed of a conductive material such as graphene or silver chloride. The electrode 50 is preferably composed of a silver chloride material.

Figure 11:
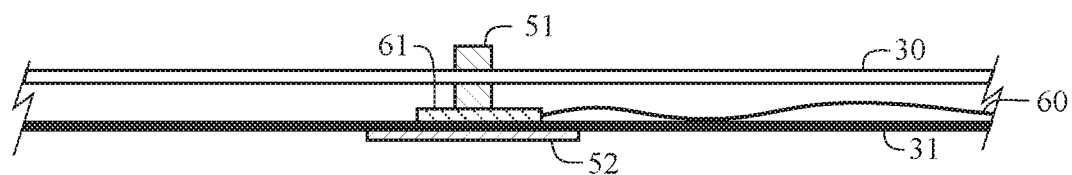
FIG. 11 is an isolated cross-sectional view of an bi-layer extension of with an electrode of an emergency cardiac and ECG electrode placement device.
Figure 11A:
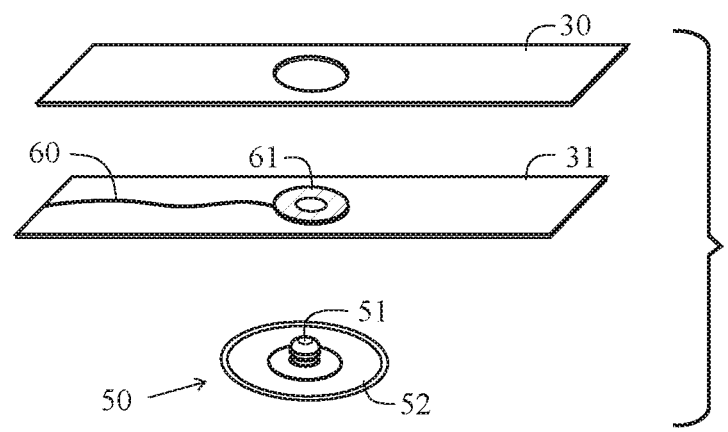
FIG. 11A is an exploded view of the extension and electrode of FIG. 11.

A bi-layer extension is shown in FIGS. 11 and 11A. Each extension member of the body 21 preferably comprises a top layer 30 composed of a flexible material and an adhesive layer 31 composed of a flexible material, with a removable backing layer attached to an adhesive surface of the adhesive layer 31. A top surface of the adhesive layer preferably includes an integrated printed wire (or elastic electrical conducting material) 60 with a connector 61. One preferred material for the flexible material is KT TAPE from Spidertech. The top layer 30 preferably has a Shore A hardness ranging from 50 to 90, which better allows for chest compressions. One preferred material for the adhesive layer is an adhesive from 3M. Each of the electrodes 50 preferably comprises a connection stud 5l and a contact pad 52. Each contact pad 52 is preferably has a diameter ranging from ("mm") to 40 mm, and most preferably 35 mm, to in one embedment allow for retention of a gel protector. Each contact pad 52 is preferably composed of a material from 3M. A cable connector 61 is connected to a connection stud 51 of each electrode 50 preferably using a conductive epoxy. Each cable connector 61 is preferably composed of 0.2 mm thick copper, with a 26 mm inside diameter.

Figure 12:
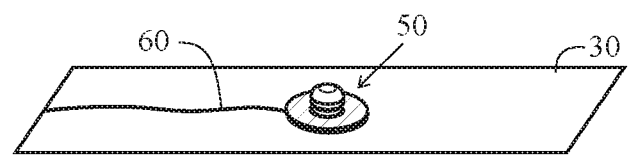
FIG. 12 is an isolated cross-sectional view of a single layer extension of with an electrode of an emergency cardiac and ECG electrode placement device.
Figure 12A:
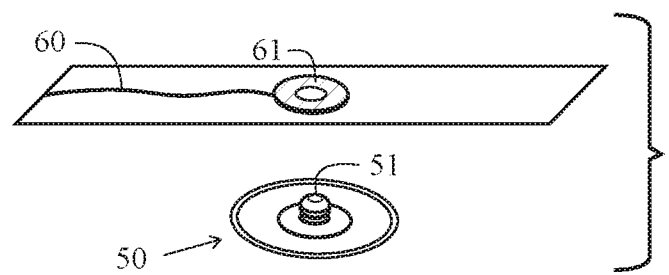
FIG. 12A is an exploded view of the extension and electrode of FIG. 12.

FIGS. 12 and 12A illustrate an isolated cross-sectional view of a single layer extension. A top surface of the main layer 30 has an integrated printed wire (or elastic electrical conducting material) 60 with a connector 61. Each electrode is attached to an adhesive surface of the main layer 30 with a stud extending through an aperture to connect to the connector 61.

Figure 13:
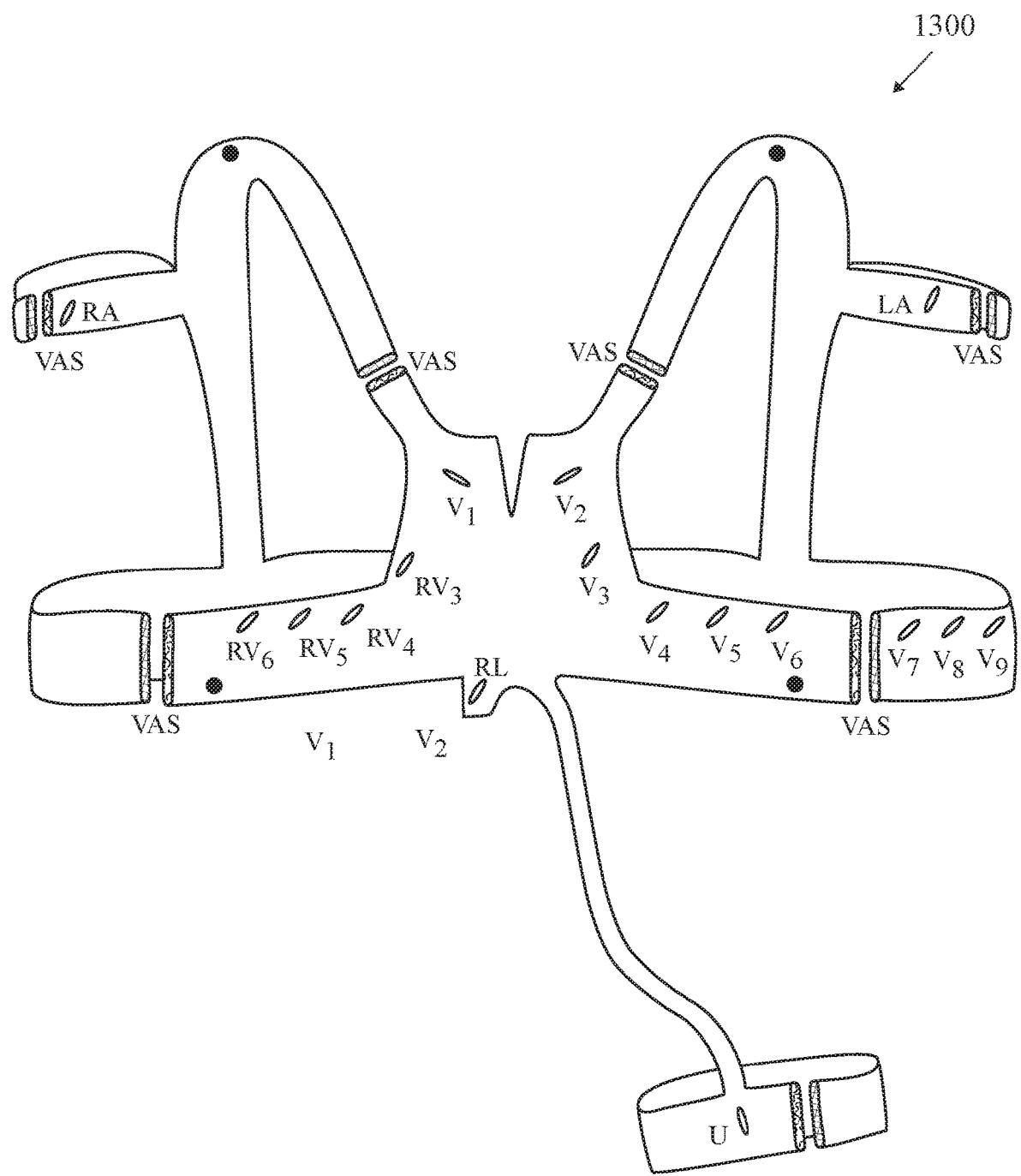
FIG. 13 is an illustration of an emergency cardiac and ECG electrode device.

FIG. 13 is an illustration of an emergency cardiac and ECG electrode device 1300.

Figure 14:
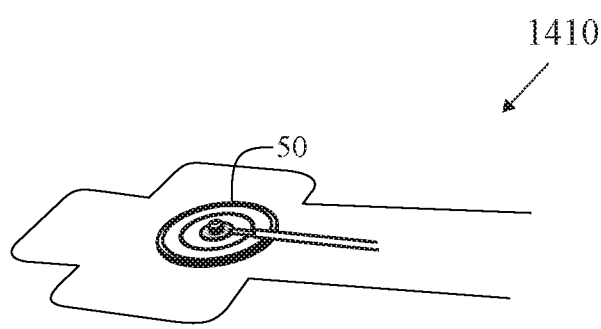
FIG. 14 is a bottom view of a component of an emergency cardiac and ECG electrode device.
Figure 14A:
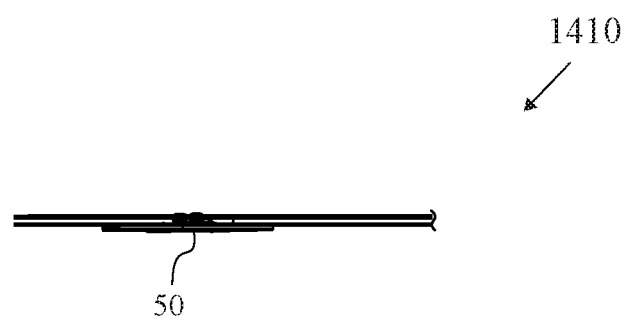
FIG. 14A is a cross-sectional view of a component of an emergency cardiac and ECG electrode device.
Figure 15:
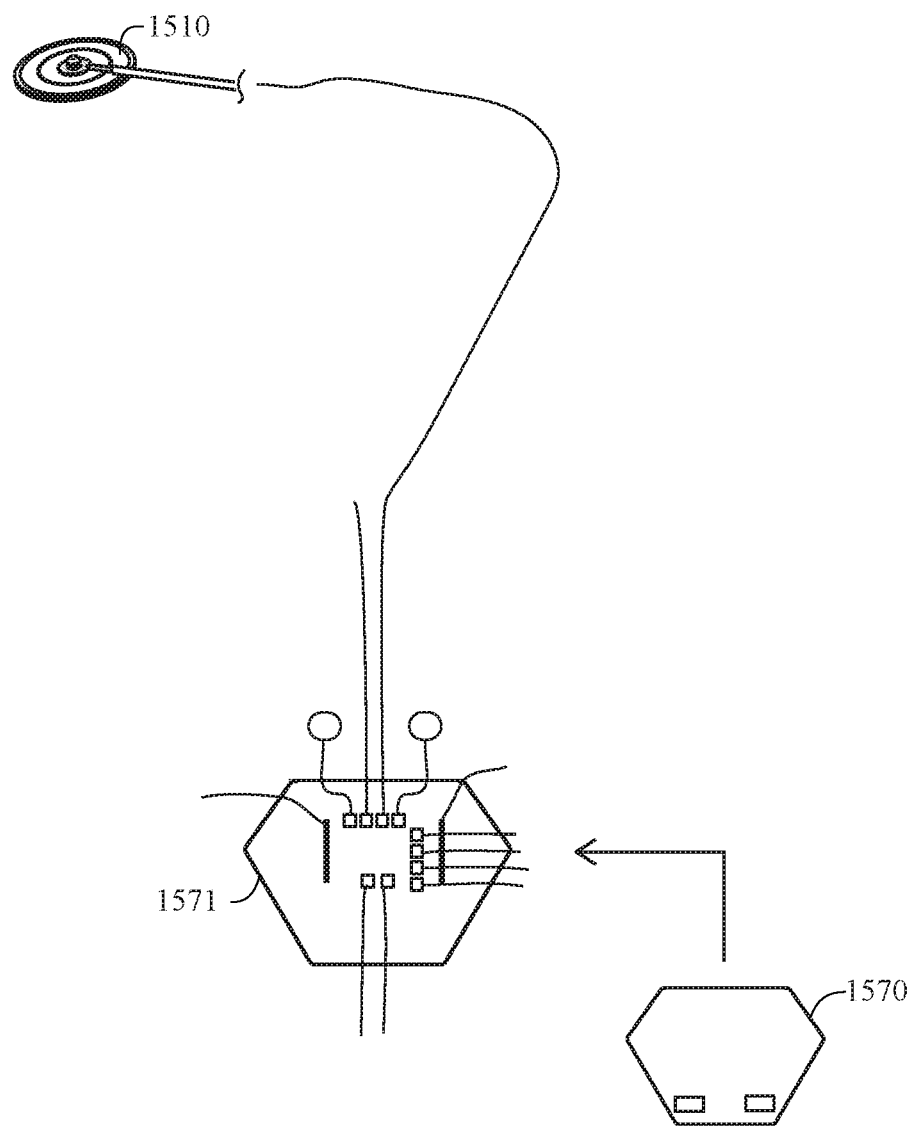
FIG. 15 is an illustration of a component of an emergency cardiac and ECG electrode device.
Figure 15A:
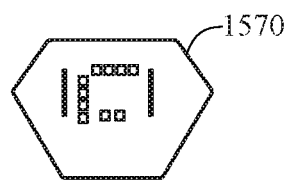

FIG. 14 is a bottom view of a component 1410 of an emergency cardiac and ECG electrode device. FIG. 14A is a cross-sectional view of a component 1410 of an emergency cardiac and ECG electrode device. An electrode 50 has an elastic conductive materials around it, preferably silver chloride and/or graphene. FIG. 15 is an illustration of the interior components for a wear garment. A printed electrode 1510 extends from a connector 1570.

Figure 16:
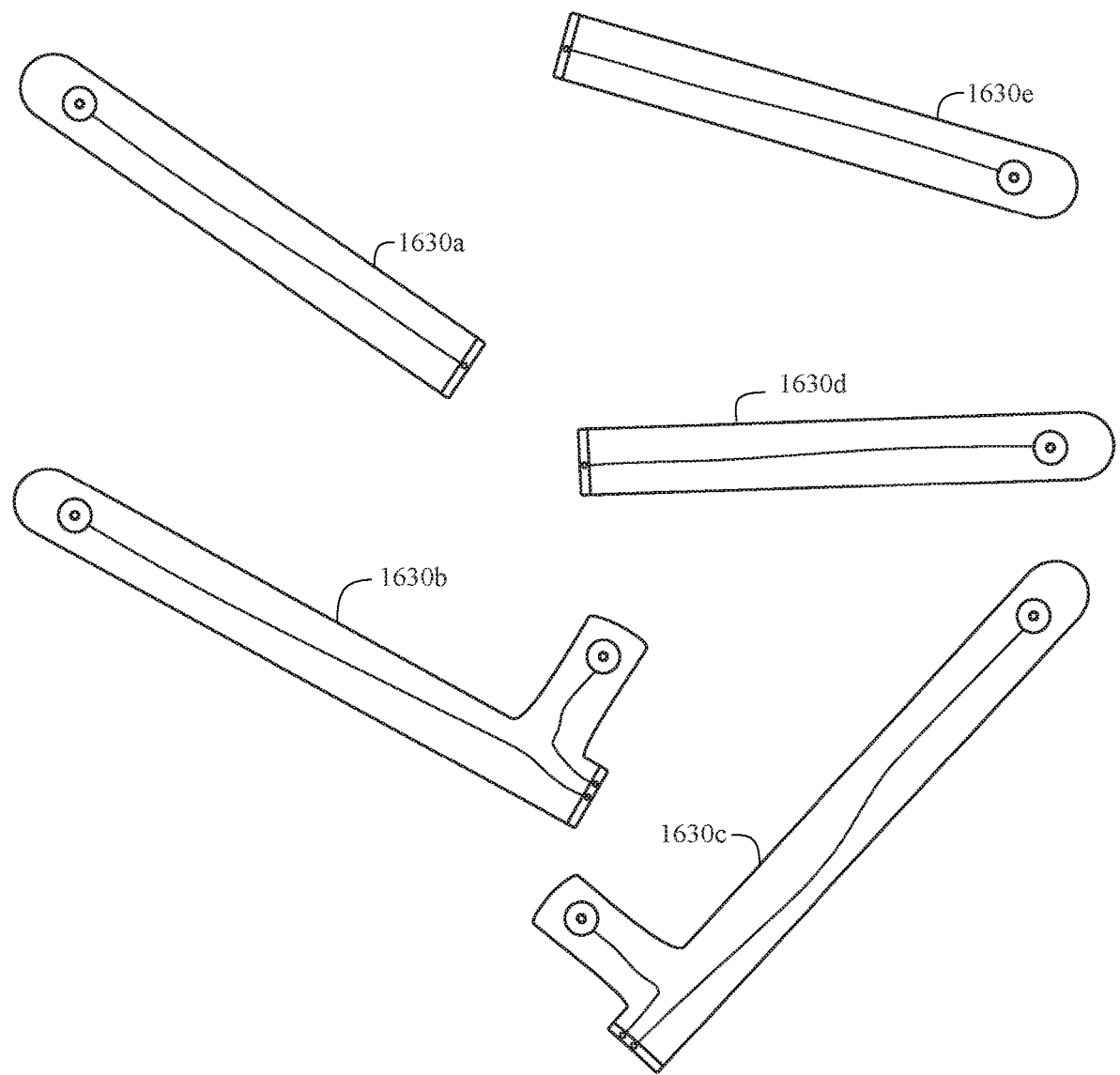
FIG. 16 is an illustration of a component of an emergency cardiac and ECG electrode device.

FIG. 16 is an illustration of components 1630a-e of an emergency cardiac and ECG electrode device.

Figure 17:
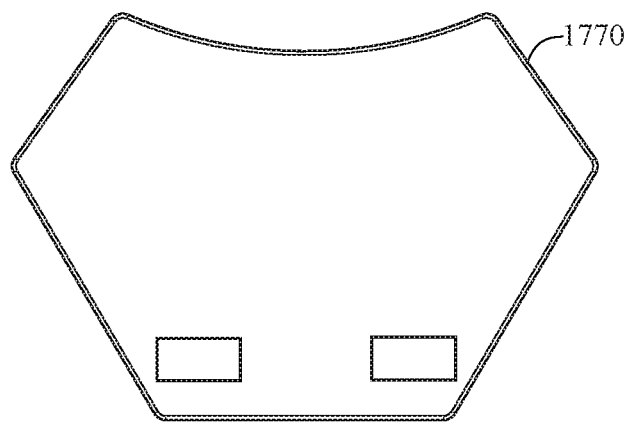
FIG. 17 is a top view of a component of an emergency cardiac and ECG electrode device.
Figure 17A:
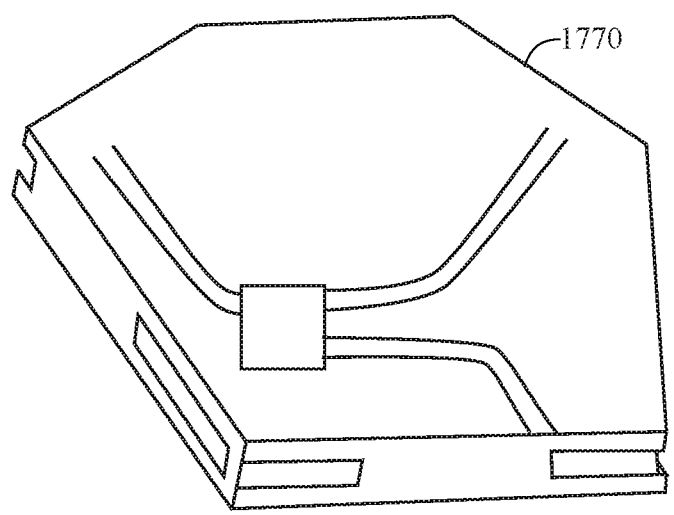
FIG. 17A is a bottom view of a component of an emergency cardiac and ECG electrode device.

FIG. 17 is a top view of a component 1770 of an emergency cardiac and ECG electrode device. FIG. 17A is a bottom view of a component 1770 of an emergency cardiac and ECG electrode device.

The EXG device 20 is preferably provided in a compact, easily stored and transported form, that is then applied to a patient's chest wall with materials that have adhesive capabilities that preferably resist moisture and conforms to the patient's body with inherent elasticity with placement of electrodes within a pad that maintain proper anatomic ratios and locations. The EXG device 20 preferably remains adherent to the patient's body through the duration of the acute pre-hospital and transition through the emergency department and acute hospitalization care periods (which is typically three days), but the EXG device 20 remains easily removable, while tolerating physiologic changes such as sweat, fever and medical treatment such as cardiac pulmonary resuscitation ("CPR"). The EXG device 20 is clearly marked and designed to fit to the chest wall so that its application ensures proper placement of all electrodes on the patient. The incorporated electrical conducting materials come together into a single cable/wire that is either directly or indirectly joined to an ECG monitoring device. The cable has adaptor capability that allows for wireless transfer of data to an ECG monitoring device obviating the need for having a bulky ECG machine in close proximity to the patient. The single cable also eliminates the need for multiple wires on a patient. Multiple wires that could potentially interfere with diagnostic imaging such as chest radiographs, or interfere with placement of emergency medical equipment such as transcutaneous cardiac pacer pads or defibrillating pad.

The EXG device 20 reduces the time to perform ECG testing significantly. With proper training, a user can anticipate ECG acquisition in less than one minute, and potentially within seconds. Current ECG data can take several minutes or longer depending on the care setting. It is not unusual for an ECG ordered in a hospital setting to take more than 10-30 minutes.

The EXG device 20 also eliminates lead transposition error. That is, the attachment of an electrode wire in a wrong electrode.

The EXG device 20 makes ECG data more reliable and reproducible. There is no variation in lead placement while performing serial ECGs—which is often done in the hospital and pre-hospital setting. The incorporated elastic electroconductive materials allow for this small form factor to accommodate varying body types (man, women, adult, child, obese, anorexic) while maintaining strict anatomic ratios and correct placement and ensure proper lead placement.

The ease of use of the EXG device 20 makes ECG acquisition less inconvenient and potentially improves ECG utilization in the pre-hospital setting.

The EXG device 20 also reduces the frequency of lead detachment.

An alternative embedment of the EXG system has wireless transfer capability that makes acquisition of the ECG in any situation feasible.

The EXG device 20 preferably incorporates either integrated elastic electro-conductive materials or printable elastic electro-conductive material used in the acquisition of electrical signals from the electrodes.

The EXG device 20 adheres to skin surfaces through a variety of physiologic conditions not currently met by current methods.

The EXG system allows for acquisition of data in settings that standard methods currently fail.

Existing technology for ECG acquisition relies on technical expertise in lead placement.

Removing technical error is dependent of operator knowledge and skill, as well as interpretation of ECG data to identify systemic error in placement.

The time to acquire an ECG is dependent on many factors but is limited due to the number of electrodes that are placed on the chest and torso, which then need to be attached to the ECG device. There are preferably a minimum of ten wires involved, and more electrodes are possible to allow for more specific views of the right side of the heart and/or posterior heart leads.

The EXG device 20 is preferably a single device with embedded lead placement through a wearable material (such as a fabric) with a small physical footprint with the elasticity to maintain physiologic measurement across different ages, gender and body habitus without requiring multiple sized devices.

The EXG device 20 solves the problem of lead detachment, lead reversal, inability to apply leads due to extremes in physiology, and lack of reproducibility to measure subtle changes. The ease of use with EXG allows for acquisition of ECGs that would not have been obtained and therefore limits the opportunity loss of delays in diagnosis and treatment. The use of an elastic pourable or printable or otherwise applied film of elastic conductive material will replace bulky standard cables and wires allowing for a more compact form, smaller footprint, and contribute to less material and weight of the device.

The EXG device 20 is a single device with embedded electrodes and elastic conductive materials to obtain standard EKG and cardiac signals with placement via a wearable fabric with a small physical footprint with the elasticity to maintain physiologic measurement across different ages, gender and body habitus without requiring multiple sized devices culminating with an output device of one single cable that is universally adaptable to all current ECG/EKG/Cardiac monitoring devices via device specific adapters.

In one embodiment, the EXG device preferably comprises: adhesive stretchable material that is breathable and water/sweat resistant; embedded elastic electroconductive material conducting electrical signals from the integrated cardiac electrodes to a central data cable; embedded elastic electroconductive material/wiring/cabling arranged to allow for stretching across body types and sizes; electrode connection port; Bluetooth capable emitter and receiver; conduction gel; and embedded electrodes (manufactured or printable).

The elastic adhesive membrane preferably provides adherence to body surface. It is preferably tolerant to moisture. The EXG device preferably incorporates electroconductive materials and electrodes that conduct signal from the skin to a single data cable/wire. The EXG device preferably expands in an elastic fashion to appropriately fit varied body types while meeting exact ratios of electrode distance without distortion. The EXG device preferably has significant stability of size and shape with elastic components to make it easily applicable to the chest wall. The EXG device preferably comes in a compact form factor.

In one embodiment, there is encapsulated expandable electroconductive material within the membrane. Within the elastic membrane is incorporated electroconductive materials that originate from each electrode to bring the cardiac electrical signal to the monitoring device via a single data cable encompassing all appropriate ECG leads. This will be a novel use of new technology using elastic electroconductive printable materials that will stretch with the electrode assembly pad and retain conductivity. Potentially use existing electroconductive materials to expand and contract with the device to deliver electrode signals to the monitoring equipment.

Alternatively, the EXG device allows for the use of external electrodes. In the event that ECG monitoring equipment is not compatible with the data cable, electrodes at the ascribed anatomical locations can be accessed with standard medical cardiac monitoring and ECG devices.

In one embodiment, there is a conductive membrane at ECG electrode sites. At the ascribed electrode ECG locations is a typical electroconductive Ag/AgCL membrane to conduct current from body surface to ECG monitoring device.

In one embodiment, a data cable brings individual electrodes into one cable that encompasses a minimum of ten wires/leads of the typical ECG analysis which is then compatible with various ECG devices and wireless transfer system. Other conductive interfaces may be utilized with the invention including ones composed of graphene/carbon, nickel, and copper.

In use, one applies the EXG device 20 to an anterior chest wall overlying the sternum symmetrically at a level above the nipple line of the patient and below the sternal notch, removing the backing layer 32 to expose the adhesive surface 31a of the adhesive layer 31. The precordial limb is then stretched to the lateral chest wall at the mid axillary line below the nipple line. Similarly each limb will have the backing layer 32 removed in succession to expose the adhesive surface 31a of the adhesive layer 31. The right upper extremity limb is stretched towards the right shoulder. The left upper extremity is stretched towards the left shoulder. The right lower extremity limb is stretched to the right lower abdominal quadrant. The left lower extremity limb is stretched to the left lower abdominal quadrant. The cable is either attached to directly to the ECG device cable. Or in versions utilizing a BLUETOOTH transceiver, then the EXG device 20 is activated to sync with the BLUETOOTH transceiver that is already connected to the ECG device.

Another embodiment has a posterior extension member which preferably has multiple electrodes that connect via a cable to an intermediary adapter module which connects to the electrode cable connector 71. The posterior leads preferably are connected through the adapter module onto the end of the original EXG device 20 and basically take over leads V5-6 for the standard ECG.

In an alternative embodiment, the EXG device 20 comprises a wireless emitter and a wireless receiver. The wireless emitter is connected to electrode cable connector 71, and the wireless receiver is connected to an ECG machine. The wireless emitter and the wireless receiver preferably operation on a BLUETOOTH communication protocol. However, those skilled in the pertinent art will recognize that other wireless communication protocols may be utilized with the alternative embodiment of the EXG device 20 without departing from the scope and spirit of the present invention.

In another embodiment, the EXG device 20 also preferably comprises a plurality of external electrodes.

The stretching capability of the extension members of the EXG device 20 preferably extends from a length L1 ranging from 7.0 to 14.0 inches to a length L2 ranging from 10.0 to 16.5 inches. In a most preferred embodiment, L1 ranges from 10 to 11 inches, and L2 ranges from 12 to 13 inches. A width of each extension member 22, 23, 24, 25, 26 preferably ranges from 1 centimeter ("cm") to 10 cm, and most preferably 2.5 cm to 5 cm. A thickness of each extension member 22, 23, 24, 25, 26 preferably ranges from 0.1 inch to 0.5 inch.

The emergency cardiac and ECG electrode placement device 20 is capable of being applied to a patient while an emergency vehicle is in motion since the device 20 is applied to and adheres to a patient's chest area, which mitigates signal loss. Likewise, the emergency cardiac and ECG electrode placement device 20 is capable of being applied to a patient that is moving due to a seizure, aggressiveness, and the like.

A preferred source for the printed wires is PE874 conductor ink from Intexar Dupont. Those skilled in the pertinent art will recognize that other printed electrically conductive materials may be used without departing from the scope and spirit of the present invention.

A conductive elastic rubber material is disclosed in U.S. Pat. No. 8,491,884, which pertinent parts are hereby incorporated by reference.

A stretchable graphene film material is disclosed in Chen et al., U.S. Patent Publication Number 20150273737, which pertinent parts are hereby incorporated by reference.

A flexible conductive material comprising silver is disclosed in Taguchi et al., U.S. Patent Publication Number 20130056249, which pertinent parts are hereby incorporated by reference.

Dunphy et al., U.S. Pat. No. 9,986,929 for an Emergency Cardiac And Electrocardiogram Electrode Placement System is hereby incorporated by reference in its entirety.

McClung et al., U.S. patent application Ser. No. 16/428,927, filed on May 31, 2019, for an Emergency Cardiac And Electrocardiogram Electrode Placement System With Artificial Intelligence is hereby incorporated by reference in its entirety.

McClung et al., U.S. patent application Ser. No. 16/428,984, filed on Jun. 1, 2019, for an Emergency Cardiac And Electrocardiogram Electrode Placement System With Wireless Electrodes is hereby incorporated by reference in its entirety.

McClung et al., U.S. Patent Application No. 62/679,879, filed on Jun. 3, 2018, for an Emergency Cardiac And Electrocardiogram Electrode Placement System With Wireless Electrodes is hereby incorporated by reference in its entirety.

Dunphy et al., U.S. Provisional Patent Application No. 62/679,856, filed on Jun. 3, 2018, for an Emergency Cardiac And Electrocardiogram Electrode Placement System With Artificial Intelligence is hereby incorporated by reference in its entirety.

McClung et al., U.S. Provisional Patent Application No. 62/679,879, filed on Jun. 3, 2018, for an Emergency Cardiac And Electrocardiogram Electrode Placement System With Wireless Electrodes is hereby incorporated by reference in its entirety.

McClung et al., U.S. Provisional Patent Application No. 62/679,876, filed on Jun. 3, 2018, for an Emergency Cardiac And Electrocardiogram Electrode Placement System With Alarm Feature is hereby incorporated by reference in its entirety.

McClung et al., U.S. Provisional Patent Application No. 62/679,022, filed on Jun. 1, 2018, for an Emergency Cardiac And Electrocardiogram Electrode Placement System With Pulse Oximeter Respiratory Rate And Temperature Monitor is hereby incorporated by reference in its entirety.

Dunphy et al., U.S. Provisional Patent Application No. 62/679,874, filed on Jun. 3, 2018, for a Pre-Hospital Artificial Intelligence Continuous EKG Reading And Interpretation System is hereby incorporated by reference in its entirety.

McClung et al., U.S. Provisional Patent Application No. 62/679,872, filed on Jun. 1, 2018, for a Strategic Cardiac Monitor is hereby incorporated by reference in its entirety.

We previous referenced our patented technology of obtaining a diagnostic ECG with a stretchable adhesive fabric utilizing a multitude of electrodes and wires to allow for adjustable sizing within a single device across most adult requirements. This device allows for both non-adhesive and adhesive electrodes to be placed via a re-useable fabric garment that has indexed positioning and capability of being washed for re-use. The garment further allows the attachment of additional physiology monitors such as blood pressure assessment and non-invasive assessment of tissue and capillary oxygenation as well as respiratory variation and pulse oximetry. Often patients are transported between locations and require bulky monitors to travel with them where this smart-garment allows for compact within garment transmission and limits the need for multiple ancillary physical monitors. Its also allows for this data to be obtained reliably at home and is pertinent to those patients who would benefit from continued at home telemetry. The device is compatible across a plethora of existing hardware and manufacturers and can be encased in water-proof material to allow for monitoring in austere environments. The device can be sized for infants as well as children and adults. The use of non-adhesive electrodes allows for multiple re-use with greater comfort and improved compliance.

The specific problem resolve by the present invention is the reliable acquisition of a diagnostic 12 lead ECG within and outside of the traditional health care setting by medically-trained persons as well as laypeople with little training is difficult. The lead positions and ability to obtain a 12 lead ECG without investing in costly equipment and training makes this important medical knowledge inaccessible to most persons unless they are in a traditional health care setting.

The present invention preferably utilizes adhesive and non-adhesive standard ECG electrodes; shielded and insulated wires for data acquisition and transfer; and stretchable garments made from combined materials such as polyester, spandex, gortex and cotton with strategically placed eyelets that allow for device attachment at specified positions for accurate physiologic monitoring.

Stretchable elastic fabric type garments that can be long or short sleeved with extension down to the proximal limb regions.

Incorporation of 10 electrode placement nodes indexed to meet AHA guidelines for diagnostic criteria 12-lead ECG and additional node positions for diagnostic studies for right sided interpretation and posterior interpretation lead positioning.

Incorporated conductive materials to transmit electrical signal from the electrodes to a central unit.

Central unit that receives all electrical signals and can be integrated with wired technology to standard ECG machines for interpretation.

Central unit that receives all electrical signals from the electrodes and be integrated into a wireless transmitter for reception by a device such as cell phone, ECG machine, cloud based system for ECG interpretation.

The method steps of the invention begin with applying pre-wired garment to anterior chest resting the center chest piece at the marked indication for the nipple line. This assures indexed positioning of the device and alignment with the precordial positions. Next, stretch the garment so it rests at least to the level just distal to the hip joint at the lower limbs and distal to the shoulder joint at the proximal limbs. Stretching the garment to the proximal limb positions having prior adequate precordial positions now satisfies the AHA guidelines for diagnostic resting ECG interpretation. Next, the left sided electrode should rest at the mid axillary line and below the nipple level when lying down. This ensures adequate lateral positioning of the device. The device can be further secured for external activity by looping a connection around the torso, neck and proximal limbs. Securing the device to the torso and limbs allows for continued monitoring during movement and/or exertion and limits the single noise induced with shifting lead positions. A modified version is incorporated into a long shirt like garment. A mother modified version includes a inner stretchable fabrics layer as described above that is conformable while an outer loos layer of cotton forms a gown typical of hospital use with closures at the neck and sides or directly with a multitude of enclosures such as tooth-in-groove binding or stud-eyelet-groove attachments.

The electrodes include a multitude of designed electrodes to improve signal to noise ratio through use of designs which limit wire movement and improved signal processing from skin electrodes which are designed with bipolar and tripolar concentric ring electrodes. These electrodes are flexible and elastic with improved spatial resolution. They are printable by methods of screen printing and methods of 3D printing directly to fabric. The design of the interface between the electrode and the lead is optioned to allow for exchange/ replacement of electrodes which offers re-usability. The flexible electronic composition allows for conformity to various body habitus while preserving the integrity of signal quality at rest and in motion.

The skin-to-electrode interface will comprise of either AgCl printed gel, graphene, or copper with overlying AgCl.

We have also specifically designed metallic electrodes meant to be covered with re-placeable AgCl covers. This allows insertion into spaces within the fabric for improved positioning, hold and removability allowing for re-use.

The printable electrode designs are included below which demonstrates an interface between the leads and the electronic components for taking the analog data and passing through either an analog connector directly to a bedside traditional ECG instrument or the option of wireless transmission with an analog-to-digital transmitter with a reciprocating receiver for connectivity to instruments or cloud-based ECG analysis.

A modular design of printable electrodes and fabric limbs with a central chest piece for index anatomical positioning and central attachment of leads for signal transmission/ connection is illustrated below. These designs indicate our intention for diagnostic ECG analysis with traditional 12-lead, 15 Lead, and Right-sided lead positions and posterior lead positions which encompasses the totality of acute diagnostic lead positioning in acute care.

The patient robe/gown will have velcro-like pulleys for compression positioning of the electrodes against the proximal limbs and across the chest and afford various height adjustments and adjustments for girth.

The ability to take population data to a granular individualized level of risk is the specific problem the EXG platform solves. Aggregate data from populations does not translate well to individual risk and this lack of specificity leads to an abundance of treatment applied to individuals that may not be of benefit and additionally adds costs that induce burden to the overall health system. Furthermore, the eXg platform will allow for AI interpretations that exceed current limitations of poor physiologic variability in exercise testing utilizing computer-interpreted ECG or segment analyses.

In another embodiment, the invention provides a data collection and repository of diagnostic-level information that is reliable and accurate for frequent re-sampling and simulation of algorithms to be applied to predict the likelihood of cardiac-related events. The threshold determination of those events defined by goodness-of-fit and explanation of variance from individualized baselines will afford the opportunity to identify an adaptive solution that improves the population-level statistic to an individual level risk of event. For instance an individual through frequent re-sampling could undergo statistical analysis via Monte-Carlo simulation fortified by confidence from resampling to serve as both collection/investigation- and validation-set of data to predict their individualized outcome of wave morphology. This type of analysis is not afforded by the current art nor performed by current computer-interpreted ECG analysis. Even in standardized cardiac exercise testing there are significant limitations to ECG-segment analysis in settings of heart block or prior injurious patterns. The EXG platform can allow for improved recognition of events in these subsets not currently covered by the existing art.

Creation of this device will reduce the time to complete an electrocardiogram (ECG) in the pre-hospital and emergency setting, eliminate systematic error in placement and interpretation of an ECG electrode, maintain and place electrodes in the proper anatomic locations across all body types, will not delay management in critical case, maintain proper skin contact through different physiologic responses such as sweat, cold and heat, as well as through medical treatment such as CPR, be easy to train providers in application and placement of ECG electrodes, and be adaptable to scenarios where space and situations limit ECG placement.

The eXg electrocardiogram system acquires cardiac electrical data on subjects. This system is in accordance with American Heart Association diagnostic quality electrode placement. The acquisition of this real time data from subjects over the course of days and months has the potential to add to our knowledge of cardiac electrical activity and its association with various physiologic conditions. Classically, the electrocardiogram (ECG or ECG) has been used to diagnose a multitude of cardiac abnormalities. Examples of such include but are not limited to: myocardial infarction (heart attack), rhythm abnormalities (eg atrial fibrillation, supraventricular tachycardia, ventricular fibrillation and many others), electrolyte disorders (potassium, calcium and others), environmental exposures, physiologic stressors such as infection, cardiac output, and toxic exposures to name a few. With the acquisition of quality electrocardiogram data with the eXg system there is potential for further development of Artificial Intelligence algorithms and analytics heretofore unexplored.

With EDAPT and the development of a database of quality electrocardiograms coupled with matched subject health informatics we anticipate the ability to develop an artificial intelligence engine that will be predictive of cardiac events with potential to mitigate morbidity and mortality. Current ECG algorithms focus on static data analysis with interpretation of ECG data based on standard concepts of electrophysiology. Development of a database of ECG information coupled to AI looks to go from interpretation of data to prediction of outcomes. EDAPT is that system.

Heretofore electrocardiogram monitoring has been studied with a multitude of leads for rhythm analysis but the diagnostic gold standard is the 12 lead ECG. In practice when an abnormal rhythm is detected this is to be followed by a 12 lead study for diagnostic purposes. The limitation of applying this monitoring across healthcare settings is the ability to have a skilled interpretation of abnormalities that are clinically relevant. The pre-existence of persistent electrical axis shift or abnormal wave morphology such as that which occurs in left bundle branch, as a single example, illustrates the added difficulty in diagnosing acute myocardial ischemia. The EXG platform would allow for a stable baseline to be ascertained from which the subtle changes of Sgarbossa criteria could be applied to recognize the onset of acute myocardial infarction through machine and deep learning methodology. More importantly the data repository that the EXG platform provides could allow for predictive analytics to be applied in real-time to forecast that someone was soon to meet the Sgarbossa criteria and thereby save time in recognizing an impending myocardial infarction which could significantly reduce the infarction time and allow for interventions that would have a downstream effect of limiting the morbid sequelae of these events with preserved cardiac output. These type of results would limit the rehabilitative requirements for patients and allow earlier return to normal activities and thereby significant improvement in quality of life adjusted metrics. The ability to use this data repository through real-time predictive analytics on an individualized level of care would provide granular decision making that is not otherwise possible without AI on a population level. There is a question in medical education where we ask the resident when tasked with interpreting an abnormal ECG, what is worth a thousand cardiologists? The answer: An old ECG. The prior recorded ECG allows for the determination of a complex abnormal current ECG to be placed into context of which waves are new or dynamic and is better than the most learned opinion of a single ECG which is why the baseline assessment is so valuable.

The EXG platform is a data collection repository from which continuous physiologic and diagnostic-level information can be re-sampled at frequencies not obtainable by current methods. The frequency of re-sampling allows for simultaneous establishment of baseline definition as well as recognizing departures from that baseline. The underlying process is recognition of standardized definitions of acute criteria suggestive of a cardiac abnormality, for example, myocardial infarction, which is similar to current algorithmic software embedded in most ECG machines. The difference in the EXG platform is that there is an analysis of beat to to beat variability and prolonged sampling and resampling to recognize the evolution of a cardiac event and then applied machine and deep learning to produce a predictive framework from which a clinical pathway can be produced to optimize care. Most importantly this data repository can allow for an exploration of clinical pathways not currently considered. For instance, patients with syncope who have abnormal ECGs are deemed at risk of a major cardiac event and admitted to hospital. Through the EXG platform we may be able to recognize not only which patients should be admitted or discharged but also have improved prediction of which patients require interventions such as pacemaker insertion. In addition the EXG platform could allow for estimations of cardiac output and current stroke volumes to estimate intravascular volume status and thereby predict need for intravenous fluid or transfusion requirements. The latter information has important implications in triaging patients to appropriate level facilities with capabilities to provide level of care appropriate to that patient at that time.

The use of diagnostic-quality analysis can also provide home users with the confidence of when it is reasonable to stay home and not pursue costly healthcare engagement. The recognition of normal, and its stability, is a key feature to determining if a patient requires referral. The EXG platform allows for optimizing performance and training. Through continuous monitoring during activity a prediction of fluid needs and periods of rest could optimize cardiac output under conditions of exercise and improve exercise tolerance and endurance. Optimizing cardiac health through analysis not currently restricted to diagnosing abnormal health but instead focused on improved health could have important implications of reducing needs for healthcare access. The EXG diagnostic level platform will allow the data to be explored to discover methods to improve cardiac health.

Using eXg device to capture data from subjects that is then transmitted to local, networked and cloud based machines.

Continuous 12 lead electrode data acquisition recorded on individual basis and compared within and between subjects for machine and deep learning method application. The repository allows for a multitude of mathematical investigations to produce complex predictive algorithms where goodness-of-fit can be applied to improve the explanation of variance within and between subjects. The adaptive learning provides expert level of interpretation on a multitude of patients undergoing simultaneous monitoring. The broadcast of this information across cloud based machines and notification to the individual subject with appropriate information and suggestions or reassurances.

The electrodes are placed in prescribed diagnostic positions via a platform of indexed positioned garments/instruments (EXG) that conform to American Heart Association and other professional expert guidelines for both resting-ECG and active ECG interpretation.

Dynamic and changing ECG morphology and data are not currently evaluated with current systems. The ability to collect and record and analyze quality ECG data over long periods of subject observation has not been heretofore easible. The eXg coupled EDAPT system will be the backbone of future AI analytics that will have the ability to predict certain cardiac events. The EDAPT system will detect physiologic changes that clinicians in normal practicing scenarios would never be able to replicate. ECG and cardiac electrophysiologic data is specifically ideal for the use of AI analytics. This is not only applied to recognition of disease but also prediction of improved performance and health.

EDAPT with the eXg system will potentially be able to predict cardiac events based on AI technology and data analysis.

Components for the invention include the following. Standardized physiologic electrodes (carbon-based, Silver-based, gold-based, Nickel-based or steel-based). Standardized wires with surrounding insulation and shielding which reduces nearby electrial interference and provides adequate protection. Adhesives or ergonomic garments that ensure relaible application of the electrodes to the skin surface. Wired connection between the electrode/wire coupling and an interpretive device (ECG machine). Standardized wireless transmitters and receivers that allow for analog to digital and digital to analog conversions to be used with ECG machines or cloud based machine analysis. Artificial Intelligence engines that provides machine and deep learning methodology to apply a multitude of ECG analysis repeatedly to individuals and groups. Computer data centers as repositories for data collected from eXg devices. Applications on internet connected smart phones that link to blue tooth and other wireless transmitters to integrate signal and data processing to the computer and cloud based data centers.

An electrode allows for the acquisition of superficial electrical activity.

A wireless electrode interface carries the electrical activity to a transmitter or device directly.

A powered transmitter is a long-life Battery Powered Wireless analog-to-analog or analog-to-digital transmission with or without amplification, or alternatively a direct powered connection between transmitter and receiver with or without amplification through a direct machine connection.

A powered receiver is a long-life Battery Powered Wireless analog-to-analog or digital-analog receiver with or without amplification.

A direct wired connector is a wire to ECG machine interface, multi-pin connector with or without amplification.

An ECG analytic device is a Cloud based or direct machine based instrument to interpret and allow display of the above data for analysis.

Artificial Intelligence is a complex mathematical analysis based on repeated sampling of the continuous ECG data and defined by standard segments of sampling (eg. 2.5 sec) then re-sampled at a multitude of frequency to allow for predictive analytics.

A stretchable garment with adaptive interface for varied electrode positioning is a stretchable and durable fabric to allow for adequate apposition of electrode to skin with appropriate integrity and indexed positioning. Also afford an interface for the wires and electrode to allow removal and reuse which affords appropriate hygiene and durability of the modular components.

Indexed center chest piece for wire management is the center chest piece allows for variable wire length and positioning to afford individualized electrode placement with a standard set of wire lengths. The chest piece is indexed to the center of the chest and the resting nipple line. Correct anatomical indexing assures the diagnostic positioning of the electrodes.

A data repository is an anonymized data set of continuously broadcast physiologic measurements on a subject level basis. The aggregate of subject data allows for population analysis as well. The data set is comprised of 12 lead analog and digital signals corresponding to the electrode positions obtained over the duration of product use. Data exists in a format commensurate with current standards for wireless data (mp3, mp4, etc.).

An alarm and light indicator is an alarm and light indicators on the device to notify a patient of a visual and auditory cue that there is a required response to the data analysis/prediction.

In a method of practicing the invention, the first step is a patient applies the EXG garment. Indexed positioning of the electrodes to position along the proximal limbs below the shoulder joint and hip joint and along the precordium as described by AHA standards for diagnostic resting ECG analysis. Next, the patient or technician connects the powered transmitter for transmission of the electrode data to a receiver. Next, the patient or technician connects the powered receiver which is individual coupling a specific transmitter to a specific receiver maintain fidelity of data receiver may be attached to a ECG-device directly or to a data transmission device like a smartphone to a cloud-based ECG analysis. Next is ECG interpretation which is 2.5 sec continuous and either 3, 6 or 12 channel simultaneous and/or immediate consecutive analysis of a multitude of wave-morphology, wave-segments, and wave intervals analysis based on published diagnostic standards. Next, is the AI interface which is repeated sampling and within individual and population level repetitive analysis of ECG interpretation with machine and deep learning methods of predictions of impending changes of wave morphology, wave segments, or wave intervals and amplitudes. Additional analysis of variance coupled with timed serial comparisons. Next is data repository which is the collection of ECG-individualized data from which we can further analyze potential clinical pathways and predictions of cardiac health and stability and/or instability.

The input of a transcutaneous electrical activity acquired from standardized electrode interface gives an output of an electrical activity transferred along the EXG system representing a reliable analog measurement of the transcutaneous-derived signal.

The input of an EXG device interface with ECG analytic device/cloud based analysis gives an output of an analog data transmitted to ECG interpretive device for diagnostic assessment of specific electrical axis of wave amplitudes, morphology and segments and intervals.

The input of Artificial Intelligence Software, resampling of defined duration and repeated assessment frequency gives an output multitude of reassessments across multiple patients simultaneously with predictive analytics and machine and deep learning application of risk prediction of significant and clinically relevant changes in wave amplitudes, morphologies, and intervals.

The input of a data repository gives an output of a large dataset of individual AI analyses summed into population level analytics to predict health outcomes on a population level and allowed refinement and investigation of individual level analytics. Temporary local repositories could be coupled with a smart-device that could later upload the data to the larger repository.

With current technology utilizing the EXG-system and artificial intelligence (AI) algorithms, the potential to expand the emergency department safely to include the waiting room is now feasible. The potential to monitor all patients with chest pain remotely and safely with diagnostic AI systems will decrease missed diagnosis, increase accuracy, and improve safety throughout the healthcare system. The EXG system coupled with a continuous 12 lead central monitoring system using patented artificial intelligence to detect subtle changes in the EKG regardless of patient location is now a reality. With application of a portable reliable and diagnostic EKG monitoring device, the EXG will interface wirelessly with a central processing unit capable of detecting subtle EKG changes dynamically and alert providers of these changes. It is a perfect blend of AI and healthcare aimed at saving lives.

Current systems evaluate patients with acute coronary syndrome with point estimate EKG and serial serum enzyme testing. Recurrent episodes of chest pain and heart attack are often missed due to delays in EKG acquisition and identification for subtle changes in the EKG. These point estimates have been the only feasible option for healthcare providers, until now. Patients at high risk for disease especially in the era of emergency department overcrowding and delays and triage and patient assessment raise the risk for morbidity and mortality. Serial assessments of ST segment and other subtle changes indicative of acute coronary syndrome are time consuming, resource consuming and not feasible with the current systems. The EXG-system, with its reliable placement, reproducible data acquisition, ease of use, mitigated motion artifact, allows diagnostic AI to monitor for subtle changes indicative of cardiac pathology continuously. The EXG-system coupled with continuous 12 lead EKG monitoring and wireless connectivity and AI processing will better identify patients with acute coronary syndrome, minimize risk of missed MI, and contribute to better patient outcomes.

The ability of AI to perform near continuous evaluation of multiple EKGs on multiple patients simultaneously is something that would be an unconventional and non-routine practice scope of any clinician. One patient could receive continuous EKGs on the order of up to 20 or more EKGs per minute. The AI engine would be able to continuously monitor multiple patients at a time with multiple EKGs done during the monitoring period, and that would not be feasible for any clinician. Imagine 20 patients undergoing 20 EKGs per minute over the course of a 20-48 hour hospital stay. Thousands of data points being continuously monitored and evaluated with diagnostic precision. This novel system approach to evaluating patients with presentations concerning for acute coronary syndrome will potentially decrease frequency of actual EKG acquisition as the AI will identify when changes occur, thus prompting repeat EKG evaluation versus predetermined arbitrary point estimate EKG acquisition. Potentially obviating need for repeat EKGs if no changes are noted. This will lead to saving lives, saving time and give clinicians increased confidence in evaluating these patients regardless of patient location.

The AI engine will receive data from a continuous signal via wireless or wired technology via the EXG device or any 12 lead continuous monitoring device attached to patient(s) to get a first EKG, second EKG and subsequent serial EKGs over set intervals that will do standard EKG interpretation but also compare second EKG and subsequent serial EKGs to the first EKG and/or baseline EKG and interpret changes. The AI engine will then be able to determine any significant changes concerning for acute coronary syndrome, arrhythmia, or other diagnostic criteria for dynamic EKG changes in the setting of acute coronary syndrome. Once changes or significant findings are made, algorithms will be in place to alert providers of these findings in real time. Data will be stored. Stored data will be available for review and integration into patient charts and records.

In summary, the EXG device will now allow diagnostic continuous 12 lead EKG monitoring easily, quickly, reliably and safely. Incorporation of the device with an AI system will decrease the risk of missed MI in the waiting room, on the patient floor, and in the emergency department. Similar benefits of an EXG-AI combination could be seen for patients who present with syncope (Sudden loss of consciousness) where the event may be related to intermittent arrhythmias that cause an unstable function of the heart and require pacemaker insertion. This EXG-AI combination essentially turns every space into a cardiac monitored space thus improving the resources for an entire hospital where patients now may wait specifically to placed on a ward with cardiac monitors as the majority of non-ICU hospital rooms do not have cardiac monitors installed.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim.

Therefore, the embodiments of the invention in which an exclusive property or privilege is claimed are defined in the following appended claims.

We claim as our invention the following:

1. A wearable diagnostic electrocardiogram (ECG) garment comprising:
   a garment body comprising a front, a back, a first sleeve, and a second sleeve wherein the garment body is composed of a material that is moisture resistant and conforms to a user's body with inherent elasticity;
   a plurality of electrodes positioned on the garment body, each of the plurality of electrodes comprising a connection stud, a contact pad interface a contact pad and a skin-to-electrode interface comprising AgCl printed gel, the plurality of electrodes comprising a first electrode and second electrode, each positioned on an upper center of the front of the garment body, a third electrode, a fourth electrode, a fifth electrode and a sixth electrode each positioned on a left side of an upper portion of the front of the garment body, a seventh electrode positioned on a lower front side of the garment body, an eighth electrode positioned on a lower portion of the garment body, and ninth electrode positioned on the first sleeve of the garment body and a tenth electrode positioned on the second sleeve of the garment body;
   an electrode connector extending from the garment body; and
   a plurality of wires positioned in the garment body, each of the plurality of wires connected from the electrode connector to an electrode of the plurality of electrodes;
   wherein the wearable diagnostic ECG garment is configured to a provide an ECG that conforms to the American Heart Association (AHA) guidelines.

2. The wearable diagnostic electrocardiogram garment according to claim 1 wherein the garment body is washable.

3. The wearable diagnostic electrocardiogram garment according to claim 1 further comprising a plurality of external electrodes.

4. The wearable diagnostic electrocardiogram garment according to claim 1 wherein the garment is a long sleeve shirt, a short sleeve shirt or a robe.

5. The wearable diagnostic electrocardiogram garment according to claim 1 further comprising a cable management module.

6. The wearable diagnostic electrocardiogram garment according to claim 1 wherein the wearable diagnostic electrocardiogram garment is a 12 lead ECG.

7. The wearable diagnostic electrocardiogram garment according to claim 1 further comprising a plurality of sensors.

8. The wearable diagnostic electrocardiogram garment according to claim 1 further comprising a wireless transmitter.

9. The wearable diagnostic electrocardiogram garment according to claim 1 wherein the plurality of electrodes is ten electrodes indexed to meet AHA guidelines for diagnostic criteria 12-lead ECG and additional node positions for diagnostic studies for right sided interpretation and posterior interpretation lead positioning.

10. A wearable diagnostic electrocardiogram (ECG) garment comprising:
    a garment body comprising a front, a back, a first sleeve, and a second sleeve;
    a plurality of electrodes positioned on the garment body, each of the plurality of electrodes comprising a connection stud, a contact pad interface a contact pad and a skin-to-electrode interface comprising AgCl printed gel, the plurality of electrodes comprising a first electrode and second electrode, each positioned on an upper center of the front of the garment body, a third electrode, a fourth electrode, a fifth electrode and a sixth electrode each positioned on a left side of an upper portion of the front of the garment body, a seventh electrode positioned on a lower front side of the garment body, an eighth electrode positioned on a lower portion of the garment body, and ninth electrode positioned on the first sleeve of the garment body and a tenth electrode positioned on the second sleeve of the garment body;

an electrode connector cable extending from the garment body;

a plurality of printed wires on the garment body, each of the plurality of printed wires connected from the electrode connector to an electrode of the plurality of electrodes;

wherein the wearable diagnostic ECG garment is configured to a provide an ECG that conforms to the American Heart Association (AHA) guidelines.

11. The wearable diagnostic electrocardiogram garment according to claim 10 wherein the garment body is washable.

12. The wearable diagnostic electrocardiogram garment according to claim 10 further comprising a plurality of external electrodes.

13. The wearable diagnostic electrocardiogram garment according to claim 10 wherein the garment is a long sleeve shirt, a short sleeve shirt or a robe.

14. The wearable diagnostic electrocardiogram garment according to claim 10 further comprising a cable management module.

15. The wearable diagnostic electrocardiogram garment according to claim 10 wherein the wearable diagnostic electrocardiogram garment is a 12 lead ECG.

16. The wearable diagnostic electrocardiogram garment according to claim 10 further comprising a plurality of sensors.

17. The wearable diagnostic electrocardiogram garment according to claim 10 further comprising a wireless transmitter.

18. The wearable diagnostic electrocardiogram garment according to claim 10 wherein the plurality of electrodes is ten electrodes indexed to meet AHA guidelines for diagnostic criteria 12-lead ECG and additional node positions for diagnostic studies for right sided interpretation and posterior interpretation lead positioning.

* * * * *